(12) United States Patent
Otake et al.

(10) Patent No.: US 10,761,158 B2
(45) Date of Patent: Sep. 1, 2020

(54) RADIO FREQUENCY COIL, MAGNETIC RESONANCE IMAGING DEVICE USING SAME, AND METHOD FOR ADJUSTING MULTI-CHANNEL RADIO FREQUENCY COIL

(71) Applicant: HITACHI, LTD., Tokyo (JP)

(72) Inventors: Yosuke Otake, Tokyo (JP); Hisaaki Ochi, Tokyo (JP); Kohjiro Iwasawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 75 days.

(21) Appl. No.: 16/075,227

(22) PCT Filed: Feb. 17, 2017

(86) PCT No.: PCT/JP2017/005896
§ 371 (c)(1),
(2) Date: Aug. 3, 2018

(87) PCT Pub. No.: WO2017/150215
PCT Pub. Date: Sep. 8, 2017

(65) Prior Publication Data
US 2019/0041476 A1 Feb. 7, 2019

(30) Foreign Application Priority Data

Mar. 4, 2016 (JP) .................. 2016-042032

(51) Int. Cl.
*G01R 33/36* (2006.01)
*G01R 33/34* (2006.01)
(Continued)

(52) U.S. Cl.
CPC ....... *G01R 33/3642* (2013.01); *G01R 33/343* (2013.01); *G01R 33/3415* (2013.01);
(Continued)

(58) Field of Classification Search
CPC .......... G01R 33/3642; G01R 33/34076; G01R 33/3415; G01R 33/343; G01R 33/365–3657
(Continued)

(56) References Cited

U.S. PATENT DOCUMENTS

| | | | |
|---|---|---|---|
| 4,987,370 A | * | 1/1991 | Leussler .......... G01R 33/34046 324/318 |
| 5,160,888 A | * | 11/1992 | Laukien ............. G01R 33/3808 324/309 |

(Continued)

FOREIGN PATENT DOCUMENTS

| JP | 2008-055169 A | 3/2008 |
|---|---|---|
| JP | 2009-534161 A | 9/2009 |

(Continued)

OTHER PUBLICATIONS

International Preliminary Report on Patentability received in corresponding International Application No. PCT/JP2017/005896 dated Sep. 13, 2018.

(Continued)

*Primary Examiner* — Patrick Assouad
*Assistant Examiner* — Demetrius R Pretlow
(74) *Attorney, Agent, or Firm* — Mattingly & Malur, PC

(57) ABSTRACT

A multichannel array coil of an MRI apparatus achieves both a wide sensitivity and low noise. An RF coil (array coil) is provided with a plurality of subcoils. Each of those subcoils is adjusted to be receivable of nuclear magnetic resonance signals, and also adjusted so that a part of current (first current) passing through one subcoil upon receipt of the signals flows into the other subcoil in the form of sub-current. A flowing direction of the first current is opposite to the flowing direction of the sub-current, and an electric field generated by the first current within a subject and an electric (Continued)

field generated by the first sub-current within the subject intensify each other in the space between a first loop coil unit and a second loop coil unit. Accordingly, noise correlation that is determined by an inner product of the electric fields is reduced, thereby achieving low noise.

15 Claims, 20 Drawing Sheets

(51) Int. Cl.
  *G01R 33/3415* (2006.01)
  *G01R 33/343* (2006.01)
  *A61B 5/055* (2006.01)
  *A61B 5/00* (2006.01)
(52) U.S. Cl.
  CPC ..... *G01R 33/34076* (2013.01); *G01R 33/365* (2013.01); *G01R 33/3657* (2013.01); *A61B 5/055* (2013.01); *A61B 5/7203* (2013.01)
(58) Field of Classification Search
  USPC .......................................................... 324/309
  See application file for complete search history.

(56) References Cited

U.S. PATENT DOCUMENTS

| | | | | |
|---|---|---|---|---|
| 5,489,847 A * | 2/1996 | Nabeshima | ...... | G01R 33/34053 324/318 |
| 5,680,047 A * | 10/1997 | Srinivasan | ......... | G01R 33/3635 324/318 |
| 5,777,474 A * | 7/1998 | Srinivasan | ....... | G01R 33/34046 324/318 |
| 2004/0061498 A1 * | 4/2004 | Ochi | .................. | G01R 33/3415 324/318 |
| 2008/0054901 A1 | 3/2008 | Eberler et al. | | |
| 2008/0297154 A1 * | 12/2008 | Otake | .............. | G01R 33/34046 324/318 |
| 2009/0009414 A1 * | 1/2009 | Reykowski | ........ | G01R 33/3415 343/742 |
| 2009/0021256 A1 * | 1/2009 | Soutome | .......... | G01R 33/34007 324/318 |
| 2009/0160441 A1 * | 6/2009 | Dohata | ............ | G01R 33/34053 324/309 |
| 2009/0230965 A1 * | 9/2009 | DeVries | ............. | G01R 33/3403 324/322 |
| 2010/0033177 A1 * | 2/2010 | Ochi | ...................... | A61B 5/055 324/307 |
| 2010/0033183 A1 * | 2/2010 | Ochi | ................ | G01R 33/34046 324/313 |
| 2011/0121834 A1 * | 5/2011 | Soutome | .............. | G01R 33/365 324/318 |
| 2011/0148415 A1 * | 6/2011 | Boskamp | ............. | G01R 33/365 324/318 |
| 2012/0262173 A1 * | 10/2012 | Soutome | .......... | G01R 33/34076 324/309 |
| 2013/0119991 A1 * | 5/2013 | Soutome | ................ | A61B 5/055 324/322 |
| 2013/0314091 A1 * | 11/2013 | Otake | .................. | G01R 33/365 324/322 |
| 2014/0002084 A1 * | 1/2014 | Han | ................... | G01R 33/3628 324/322 |
| 2014/0125339 A1 * | 5/2014 | Lee | .................... | G01R 33/3415 324/319 |
| 2014/0253126 A1 * | 9/2014 | Habara | .............. | G01R 33/3415 324/322 |
| 2015/0177346 A1 * | 6/2015 | Mazurewitz | ..... | G01R 33/34084 324/309 |
| 2017/0146622 A1 * | 5/2017 | Yang | .................. | G01R 33/3628 |
| 2017/0254864 A1 * | 9/2017 | Otake | ................... | A61B 5/055 |

FOREIGN PATENT DOCUMENTS

| | | |
|---|---|---|
| JP | 2013-530019 A | 7/2013 |
| WO | 2007/124247 A1 | 11/2007 |
| WO | 2012/003211 A1 | 1/2012 |
| WO | 2013/065480 A1 | 5/2013 |

OTHER PUBLICATIONS

Roemer, et al, "The NMR Phased Array", Journal of Magnetic Resonance in Medicine, 1990, vol. 16, p. 192-225.
International Search Report of PCT/JP2017/005896 dated May 23, 2017.

* cited by examiner (a) COMPARATIVE EXAMPLE (b) PRESENT EMBODIMENT (c)

RADIO FREQUENCY COIL, MAGNETIC RESONANCE IMAGING DEVICE USING SAME, AND METHOD FOR ADJUSTING MULTI-CHANNEL RADIO FREQUENCY COIL

TECHNICAL FIELD

The present invention relates to a magnetic resonance imaging (MRI) apparatus, and more particularly, it relates to a radio frequency coil (RF coil) for applying an RF magnetic field and for detecting a nuclear magnetic resonance signal.

BACKGROUND ART

An MRI apparatus utilizes a nuclear magnetic resonance phenomenon to create an image from any cross section traversing a subject. Specifically, such an MRI apparatus applies an RF magnetic field to a subject placed in a spatially homogeneous magnetic field (static magnetic field), causing nuclear magnetic resonance to occur, detects nuclear magnetic resonance signals being generated, and performs an imaging process on the signals thus detected, whereby a tomographic image is acquired.

A device that applies the RF magnetic field to the subject, and detects the nuclear magnetic resonance signals generated from the subject, is referred to as a radio frequency coil (hereinafter, referred to as an RF coil). The RF coil is provided with a loop unit (coil loop) for performing application and detection of the RF magnetic field. The smaller is the coil loop, the higher is the sensitivity of the coil, though its sensitivity region becomes narrower. On the other hand, when the coil loop is made larger, the sensitivity region can be expanded. Accordingly, in the RF coil, there are tradeoffs between the sensitivity level and the size of the sensitivity region. In addition, since the nuclear magnetic resonance signals are rotating-magnetic-field signals that are generated in the direction vertical to the static magnetic field, it is preferable to place the RF coil in the orientation allowing application and detection of the magnetic field to be vertical to the static magnetic field.

As discussed above, the sensitivity of the RF coil is enhanced with reduction of the size thereof, whereas the sensitivity region becomes narrower. As a technique to solve this problem, there is disclosed a multichannel array coil comprising RF coils small in diameter with high sensitivity, arranged in arrays (see Non Patent Document 1, for example). Since the multichannel array coil is high in sensitivity and provided with a wide sensitivity region, allowing acquisition of an image with a high SNR (Signal to Noise Ratio), currently, it serves as a dominating receiver RF coil. In the following description, each of the RF coils constituting the multichannel array coil will be referred to as a subcoil.

In general, when the RF coils having the same resonance characteristics are placed adjacent to each other, they interfere with each other due to magnetic coupling. Since performance of the RF coil is deteriorated due to the magnetic coupling, it is imperative to remove the magnetic coupling between the subcoils in the multichannel array coil. The Non Patent Document 1 discloses that the adjacent subcoils are placed in a manner that a part of the coil loop overlaps on another coil loop, thereby minimizing the magnetic coupling. Furthermore, a low-input preamplifier, an inductor, and a capacitor are used, so as to render a part of the coil loop to be high impedance, and interference from anything other than the subcoils can be reduced.

The Patent Document 1 and the Patent Document 2 disclose techniques where a decoupling means is provided in a multichannel coil, whereby magnetic coupling between the subcoils constituting the multichannel coil is reduced.

PRIOR ART DOCUMENT

Patent Document

Patent Document 1
Japanese Unexamined Patent Application Publication (Translation of PCT Application) No. 2013-530019
Patent Document 2
Japanese Unexamined Patent Application Publication (Translation of PCT Application) No. 2009-534161

Non Patent Document

Non Patent Document 1
Roemer P B, et al., "The NMR phased array", Journal of Magnetic Resonance, USA, 1990, 16, p. 192-225

DISCLOSURE OF THE INVENTION

Problems to be Solved by the Invention

With the configuration of multichannel, even though a high signal strength is obtained, noise may be increased simultaneously. Noise of the RF coil is mainly thermal noise of the subject, and this is Gaussian noise. Upon creating a composite image, noise is increased along with increasing the number of channels being combined. Therefore, in the multichannel coil, in some cases, the SNR of the image may not be improved, even though the signal strength gains with the increase of the number of channels.

Furthermore, in the array coil, multiple RF coils are placed covering the subject, and there may occur noise correlation due to electromagnetic coupling between the RF coils via the subject. The stronger is the noise correlation, the more increases the noise of the composite image.

However, the conventional multichannel techniques aim at achieving an arrangement that is optimum for avoiding loss of sensitivity at each channel, and optimization (minimization) of noise has not been addressed. In addition, magnetic coupling removal for implementing the multichannel coil intends to reduce the magnetic coupling as much as possible, but complete removal thereof is not the goal. Therefore, with the combination of the subcoils placed at positions where the magnetic coupling occurs intensively, there should remain considerable magnetic coupling, and signal strength in the multichannel coil may be lowered.

There is an image reconstruction method for minimizing noise by using noise correlation, but in the case where the noise correlation is not obtained correctly or the SNR is low, this method may turn to reduction of the SNR instead.

The present invention has been made in view of the situations as described above, and the present invention is directed to a multichannel array coil of an MRI apparatus, achieving both a wide sensitivity region and high sensitivity at deep levels, without complex configurations, and further reducing noise, whereby providing a high quality image.

Means for Solving the Problems

The present invention provides an RF coil (array coil) for an MRI apparatus, the RF coil having multiple subcoils and being placed and adjusted in a manner that an electric field generated in a subject by current passing through the subcoils may operate to reduce mutual noise between the subcoils. Specifically, at least two subcoils among the multiple subcoils are coupled electromagnetically, so that a part of the current passing through a loop coil unit of one subcoil is made to pass through the loop coil unit of the other subcoil, in the form of sub-current, and circuit components of each subcoil and an amount of electromagnetic coupling between the subcoils are adjusted so that the current passing through the loop coil unit of one subcoil is tuned to the sub-current passing through the other subcoil, and the current flows in the direction opposite to the direction of the sub-current.

Advantage of the Invention

According to the present invention, noise is reduced in the array coil of the MRI apparatus, whereby a high quality image can be obtained.

BEST MODE FOR CARRYING OUT THE INVENTION

Figure 1:
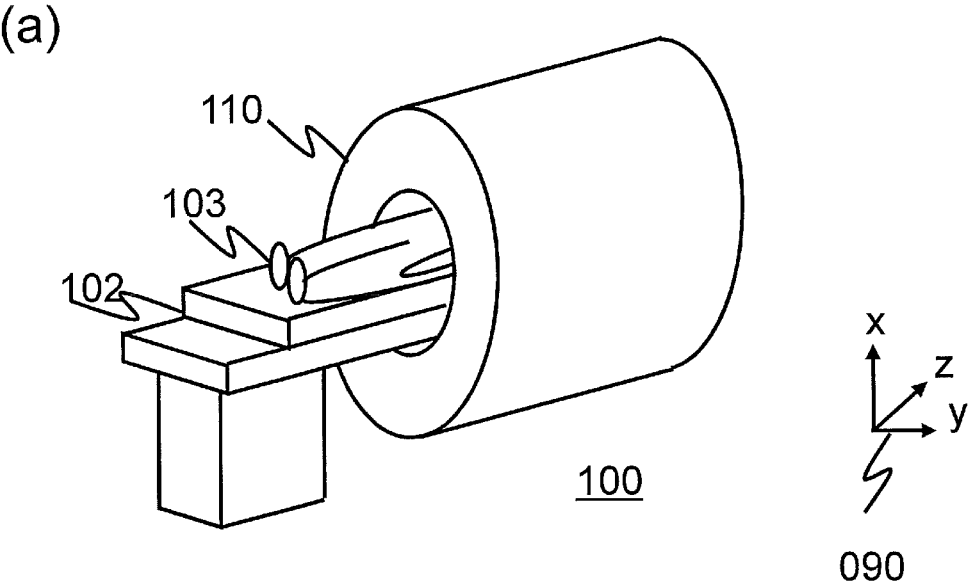
FIG. 1(a) and FIG. 1(b) are external views of an MRI apparatus.
Figure 1:
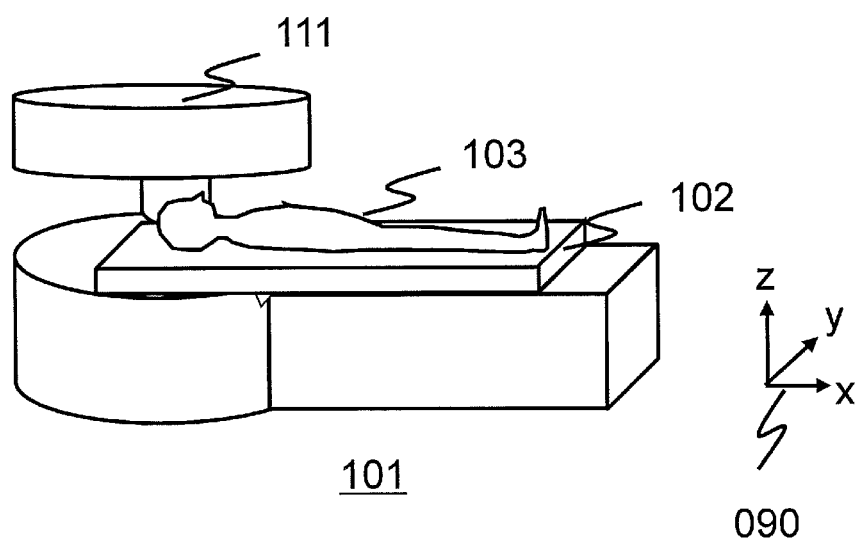

There will now be described embodiments of an MRI apparatus and an RF coil according to the present invention, with reference to the accompanying drawings. Hereinafter, in all the figures illustrating the embodiments of the present invention, components with an identical function are labeled with the same reference numeral, and they will not be redundantly explained.

<Embodiments of the MRI Apparatus>

There will be described the embodiments of the MRI apparatus to which the present invention is applied. The MRI apparatus of the present embodiments features that a specific multichannel RF coil is employed as a receiver RF coil.

[Configuration of the Apparatus]

With reference to FIG. 1, there will now be described an overall configuration of the MRI apparatus of the present embodiment. FIG. 1 is an external view of the MRI apparatus of the present embodiment. FIG. 1(a) illustrates the MRI apparatus 100 of a horizontal magnetic field system that uses a tunnel-type magnet for generating a static magnetic field by a solenoid coil. FIG. 1(b) illustrates the MRI apparatus 101 of a hamburger-type (open-type) vertical magnetic field system in which the magnets 111 are separated vertically so as to enhance a sense of openness. Each of these MRI apparatuses 100 and 101 are provided with a table 102 for placing an examinee (subject) 103 thereon. The subject 103 placed on the table is put in the space for examination where homogeneous magnetic field (static magnetic field) is generated by magnet 110 or 111. The magnet 110 or 111 constitutes a static magnetic field former that forms the static magnetic field.

The present embodiments are applicable to any of the MRI apparatus 100 of the horizontal magnetic field system and the MRI apparatus 101 of the vertical magnetic field system. The types of the MRI apparatus as shown in FIG. 1 are just examples, and any publicly-known various MRI apparatuses may be used for the present invention, regardless of modes or types of the apparatus. In the description below, as a coordinate system commonly used in any of the horizontal magnetic field system and the vertical magnetic field system, the coordinate system 090 will be employed, where a direction of the static magnetic field is indicated as z-direction, and two directions orthogonal thereto are indicated as x-direction and y-direction, respectively. In the following, this is similarly applied to all the figures in association with the present specification.

Figure 2:
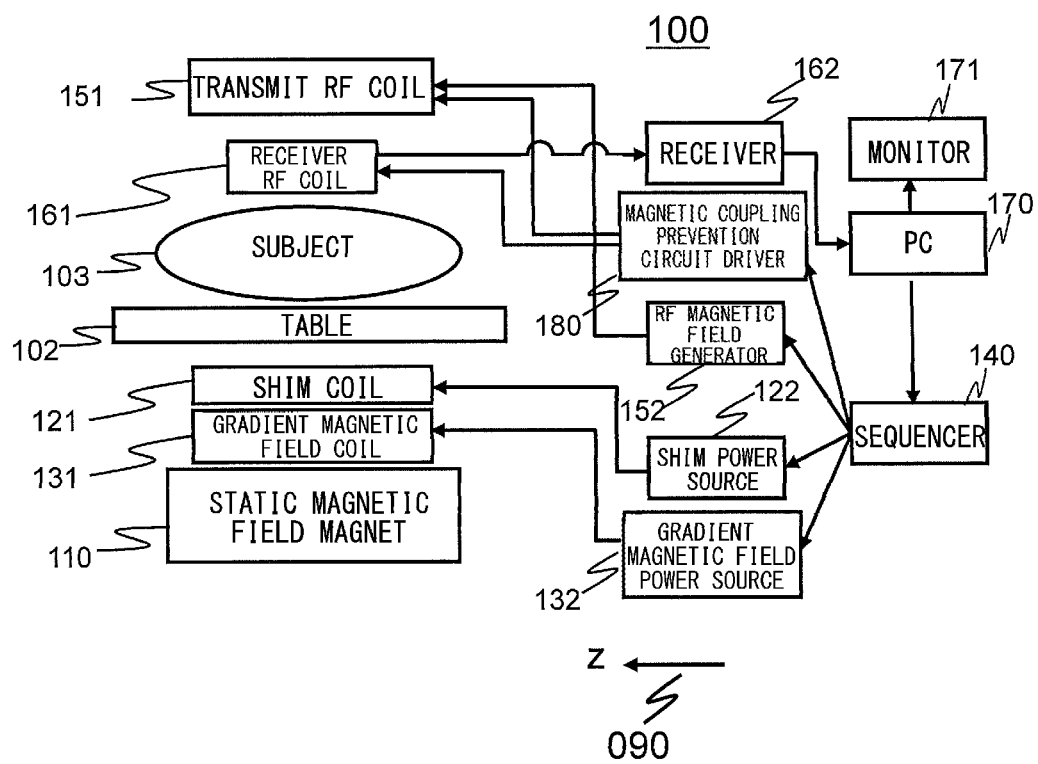
FIG. 2 is a block diagram showing a schematic configuration of the MRI apparatus.

Next, a schematic configuration of the MRI apparatus 100 will be described, taking the MRI apparatus of the horizontal magnetic field system as an example. FIG. 2 is a block diagram showing the schematic configuration of the MRI apparatus. As illustrated, the MRI apparatus 100 is provided with the magnet 110 of the horizontal magnetic field system, a gradient magnetic field coil 131, a transmit RF coil 151, a receiver RF coil 161, a gradient magnetic field power source 132, a shim coil 121, a shim power source 122, an RF magnetic field generator 152, a receiver 162, a magnetic coupling prevention circuit driver 180, a computer (PC) 170, a sequencer 140, and a monitor 171. The reference numeral 102 represents the table for placing the subject 103 thereon.

The gradient magnetic field coil 131 is connected to the gradient magnetic field power source 132, and generates a gradient magnetic field. The gradient magnetic field coil 131 and the gradient magnetic field power source 132 constitute a gradient magnetic field former that forms the gradient magnetic field. The shim coil 121 is connected to the shim power source 122, and controls a degree of homogeneity in the magnetic field. The transmit RF coil 151 is connected to an RF magnetic field generator 152, and applies (transmits) an RF magnetic field to the subject 103. The receiver RF coil 161 is connected to the receiver 162, and receives nuclear magnetic resonance signals from the subject 103. The magnetic coupling prevention circuit driver 180 is connected to a magnetic coupling prevention circuit (described below). The magnetic coupling prevention circuit being connected to each of the transmit RF coil 151 and the receiver RF coil 161, is a circuit for preventing magnetic coupling between the transmit RF coil 151 and the receiver RF coil 161.

The sequencer 140 sends commands, respectively to the gradient magnetic field power source 132, to the RF magnetic field generator 152, and to the magnetic coupling prevention circuit driver, so as to operate those units. The commands are transmitted according to instructions from the computer (PC) 170. Further according to the instructions from the computer (PC) 170, a magnetic resonance frequency is set as a reference of detection at the receiver 162. By way of example, according to the command from the sequencer 140, the RF magnetic field is applied to the subject 103 via the transmit RF coil 151. By applying the RF magnetic field, nuclear magnetic resonance signals are generated from the subject 103. Then, the receiver RF coil 161 detects thus generated nuclear magnetic resonance signals, and detection is performed in the receiver 162.

The computer (PC) 170 performs control on the overall operations and various signal processing in the MRI apparatus 100. For example, the computer receives signals detected by the receiver 162 via an A/D converter, and performs signal processing such as image reconstruction (functions of an image reconstructor). Results of the processing above are displayed on the monitor 171. Detected signals and measuring conditions are stored in a storage medium as necessary. Furthermore, the computer allows the sequencer 140 to send out commands so that each unit operates at a timing and strength programmed in advance. In addition, if it is necessary to adjust the degree of homogeneity in the static magnetic field, the sequencer 140 sends commands to the shim power source 122, allowing the shim coil 121 to adjust the degree of homogeneity in the magnetic field.

[Overviews of the Transmit RF Coil and the Receiver RF Coil]

As described above, the MRI apparatus of the present embodiment employs two types of RF coil; the transmit RF coil 151 and the receiver RF coil 161. One RF coil may serve as both the transmit RF coil 151 and the receiver RF coil 161, or independent RF coils may be used respectively.

Details of the RF coils will be described in the following, taking as an example that the transmit RF coil 151 and the receiver RF coil 161 are independent RF coils, and the transmit RF coil 151 is a birdcage-like shape RF coil (birdcage RF coil), and the receiver RF coil 161 is a multichannel array coil comprising multiple subcoils.

Figure 3:
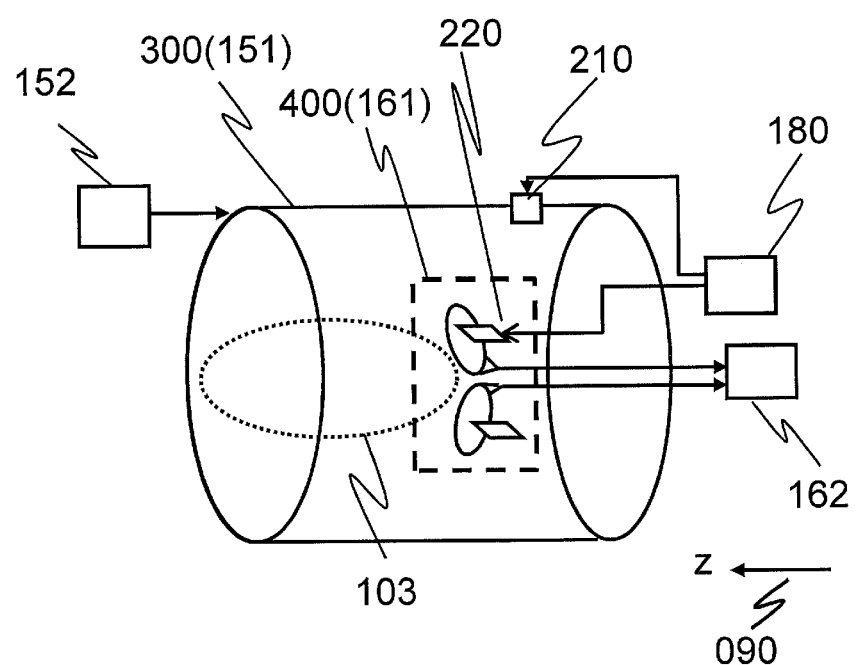
FIG. 3 illustrates a connection between a transmit RF coil and a receiver RF coil in the MRI apparatus according to an embodiment.

Firstly, with reference to FIG. 3, there will be described an arrangement of the birdcage RF coil 300 used as the transmit RF coil 151 and the array coil 400 used as the receiver RF coil 161, together with describing a connection mode of the birdcage RF coil 300, the array coil 400, the RF magnetic field generator 152, the receiver 162, and the magnetic coupling prevention circuit driver 180.

As illustrated, the birdcage RF coil 300 has an approximately cylindrical outer shape (including an elliptic cylinder or a polygonal column), and this approximate cylinder is placed to be coaxial with the central axis of the magnet 110 (the axis in the Z-direction). The subject 103 is placed inside the birdcage RF coil 300. The array coil 400 is arranged in proximity to the subject 103 within the birdcage RF coil 300. As described above, the birdcage RF coil 300 is connected to the RF magnetic field generator 152. The array coil 400 is connected to the receiver 162.

In addition, the birdcage RF coil 300 is provided with a magnetic coupling prevention circuit 210 for preventing magnetic coupling with the array coil 400, and the array coil 400 is provided with a magnetic coupling prevention circuit 220 for preventing magnetic coupling with the birdcage RF coil 300. They are referred to as transmit-receive magnetic coupling prevention circuits. Those transmit-receive magnetic coupling prevention circuits enable transmission of the RF magnetic field and reception of the nuclear magnetic resonance signals, without magnetic coupling in the arrangement as described above.

[Transmit RF Coil]

Figure 4:
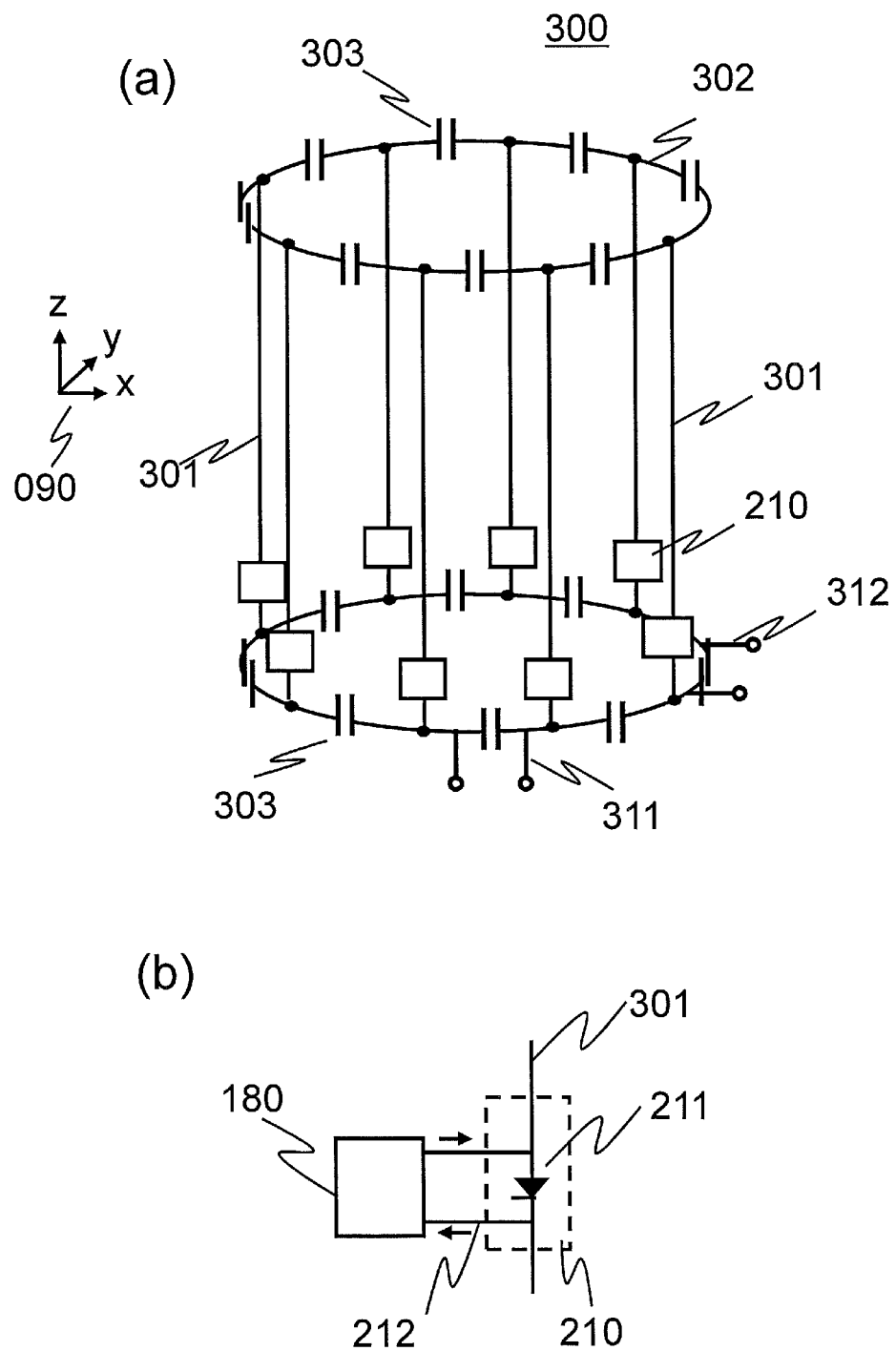
FIG. 4(a) illustrates a configuration of a birdcage RF coil that is used as the transmit RF coil.
FIG. 4(b) illustrates one example of a transmit-receive magnetic coupling prevention circuit of the transmit RF coil.

Next, with reference to FIG. 4, the birdcage RF coil 300 used as the transmit RF coil 151 of the present embodiment will be described. In the birdcage RF coil 300 according to the present embodiment, a resonance frequency is tuned to the resonance frequency (magnetic resonance frequency) of an element targeted for excitation, and the RF magnetic field at this magnetic resonance frequency is applied. In the present embodiment, the resonance frequency is tuned to the magnetic resonance frequency of hydrogen nucleus, allowing hydrogen nucleus to be excited. Hereinafter, the magnetic resonance frequency of the RF magnetic field to be applied is indicated as f0.

FIG. 4(a) is a block diagram illustrating a configuration of the birdcage RF coil 300 according to the present embodiment. As illustrated, the birdcage RF coil 300 of the present embodiment comprises multiple linear conductors 301, end conductors 302 for connecting the ends of each of the linear conductors 301, and capacitors 303 inserted in the end conductors 302.

In addition, the birdcage RF coil 300 is provided with two input ports 311 and 312. It is configured such that transmitted signals, 90 degrees out of phase with each other, are inputted into the first input port 311 and into the second input port 312, respectively, allowing the RF magnetic field to be efficiently applied to the subject 103.

In the birdcage RF coil 300 of the present embodiment, the transmit-receive magnetic coupling prevention circuits 210 for preventing magnetic coupling with the receiver RF coil 161 (array coil 400) are inserted, respectively in series with the linear conductors 301 of the birdcage RF coil 300.

As shown in FIG. 4(b), for example, the transmit-receive magnetic coupling prevention circuit 210 may comprise a PIN diode 211 inserted in series with the linear conductor 301, and control signal lines 212 are connected respectively to both ends of the PIN diode. The control signal lines 212 are connected to the magnetic coupling prevention circuit driver 180. Preferably, a choke coil (not illustrated) may be inserted into the control signal line 212, so as to avoid mixture of high frequencies.

The PIN diode 211 possesses properties that it normally indicates high resistance (OFF), and when a value of direct current flowing in the forward direction of the PIN diode 211 becomes a certain amount or more, it mostly indicates conductive (ON). In the present embodiment, such properties are utilized to control ON/OFF of the PIN diode 211, according to the direct current outputted from the magnetic coupling prevention circuit driver 180. In other words, when RF signals are transmitted, control current is made to flow to render the PIN diode 211 to be conductive via the control signal lines 212, whereby the birdcage RF coil 300 functions as the transmit RF coil 151. On the other hand, when nuclear magnetic resonance signals are received, the control current is suspended, whereby the birdcage RF coil 300 becomes high impedance, and changed to an open state.

As thus described, in the present embodiment, controlling of the direct current (control current) from the magnetic coupling prevention circuit driver 180 allows the birdcage RF coil 300 to function as the transmit RF coil 151 upon transmitting RF signals, whereas upon receiving nuclear magnetic resonance signals, the birdcage RF coil is changed to the open state, thereby removing magnetic coupling with the array coil 400 that serves as the receiver RF coil 161.

[Receiver RF Coil]

Next, with reference to FIG. 5, there will be described the array coil 400 used as the receiver RF coil 161 of the present embodiment. For ease of explanation, an array coil where two loop-shaped RF coils (surface coils) are placed side by side will be described as an example. However, any multi-channel RF coil with an arrangement of multiple subcoils is applicable as the receiver RF coil of the present embodiment, and the number of subcoils is not limited to a particular number.

As shown in FIG. 5(a), the array coil 400 of the present embodiment comprises two subcoils 410. The two subcoils 410 constituting the array coil 400 are referred to as a first subcoil 410A and the second subcoil 410B, respectively. If there is no need to particularly identify each of the subcoils 410 as components of the array coil 400, the alphabet attached to the end of the reference numerals may be omitted (the same shall apply hereafter). The first subcoil 410A and the second subcoil 410B are surface coils, each having a loop structured on an approximate plane, and there is provided a means (an electromagnetic coupler) 450 therebetween for coupling the two subcoils, electrically, magnetically, or electromagnetically. Functions and details of the electromagnetic coupler 450 will be described later.

Each of the two subcoils 410A and 410B is adjusted to be able to receive nuclear magnetic resonance signals from elements that can be excited by the birdcage RF coil 300, and each subcoil functions as one channel. Signals received by the first subcoils 410A and 410B respectively are transferred to the receiver 162.

Since the configurations of the two subcoils 410A and 410B are identical, only the configuration of the first subcoil 410A will be described below as a representative example. The first subcoil 410A comprises a loop coil unit 420 (a first loop coil unit 420A) for detecting nuclear magnetic resonance signals (RF magnetic field), a low-input impedance signal processing circuit 430 (a first low-input impedance signal processing circuit 430A), and an electromagnetic coupling adjuster 441 (a first electromagnetic coupling adjuster 441A) for connecting the loop coil unit 420 with the low-input impedance signal processing circuit 430, and the first subcoil 410A is connected to the receiver 162 via the low-input impedance signal processing circuit 430. The electromagnetic coupling adjuster 441 may comprise at least either of a capacitor and an inductor.

A loop section of the first loop coil unit 420A (the first loop 421A) is formed of conductor. Then, the first loop coil unit 420A is provided with a capacitor 424A that is inserted in series with an inductor component of the first loop 421A. This inductor component and the capacitor 424A constitute a parallel resonant circuit. In order to distinguish the capacitor 424A from other capacitors, it is referred to as a parallel capacitor 424 (a first parallel capacitor 424A).

In addition, a capacitor 422A for adjusting a resonance frequency and the transmit-receive magnetic coupling prevention circuit 220 are inserted in series with the first loop 421A. In order to distinguish the capacitor 422A from other capacitors, it is referred to as a series capacitor 422 (a first series capacitor 422A). Here, there will be described an example where two first series capacitors (422A) are provided, but any number at least one may be applicable as the number of the first series capacitors.

As described so far, the first subcoil 410A is provided with, as circuit components for adjustment, the first electromagnetic coupling adjuster 441A, the first series capacitors 422A inserted in series with the inductor component of the first loop 421A, and the first parallel capacitor 424A that is inserted in series with the inductor component, rendering the first loop coil unit 420A to serve as the parallel resonant circuit. Similarly, the second subcoil 410B is provided with, as circuit components for adjustment, a second electromagnetic coupling adjuster 441B, a second series capacitors 422B inserted in series with the inductor component of a second loop 421B, and a second parallel capacitor 424B that is inserted in series with the inductor component, rendering the second loop coil unit 420B to serve as the parallel resonant circuit.

One terminal of the low-input impedance signal processing circuit 430, provided on the loop coil unit 420 side, is connected to one end of the parallel capacitor 424 of the loop coil unit 420 via the electromagnetic coupling adjuster 441. The other terminal of the low-input impedance signal processing circuit 430, provided on the loop coil unit 420 side, is connected directly to the other end of the parallel capacitor 424 of the loop coil unit 420.

The transmit-receive magnetic coupling prevention circuit 220 removes magnetic coupling with the birdcage RF coil 300 being the transmit RF coil 151. By way of example, as shown in FIG. 5(b), the transmit-receive magnetic coupling prevention circuit 220 may comprise a capacitor 423 that is inserted in series with the conductor constituting the loop 421, the PIN diode 221 connected in parallel with the capacitor 423, and the inductor 222. Control signal lines 223 may be connected to both ends of the PIN diode 221. Furthermore, the control signal lines 223 may be connected to the magnetic coupling prevention circuit driver 180. Preferably, a choke coil (not illustrated) may be inserted into the control signal line 223, so as to avoid mixture of high frequencies. The inductor 222 and the capacitor 423 are adjusted so that they resonate in parallel at a frequency of the received nuclear magnetic resonance signals.

Generally, the parallel resonant circuit has characteristics of becoming high impedance (high resistance) at the resonance frequency. Therefore, when the current passes through the PIN diode 221, the PIN diode 221 is turned on, and the capacitor 423 of the loop 421 becomes resonant in parallel with the inductor 222 at the frequency of the received nuclear magnetic resonance signals, resulting in that the capacitor 423 becomes high impedance. Therefore, at the frequency of thus received nuclear magnetic resonance signals, a part of the loop coil unit 420 becomes high impedance, turned to be in an open state, and then, the subcoil 410 having the loop coil unit 420 is also turned to be in the open state.

As thus described, current passes through the PIN diode 221 and it is turned on, whereby the magnetic coupling between each of the subcoils 410A and 410B, and the birdcage RF coil 300 is removed. Accordingly, the magnetic coupling is also removed between the array coil 400 comprising the subcoils 410 each functioning as a coil element, and the birdcage RF coil 300.

Figure 5:
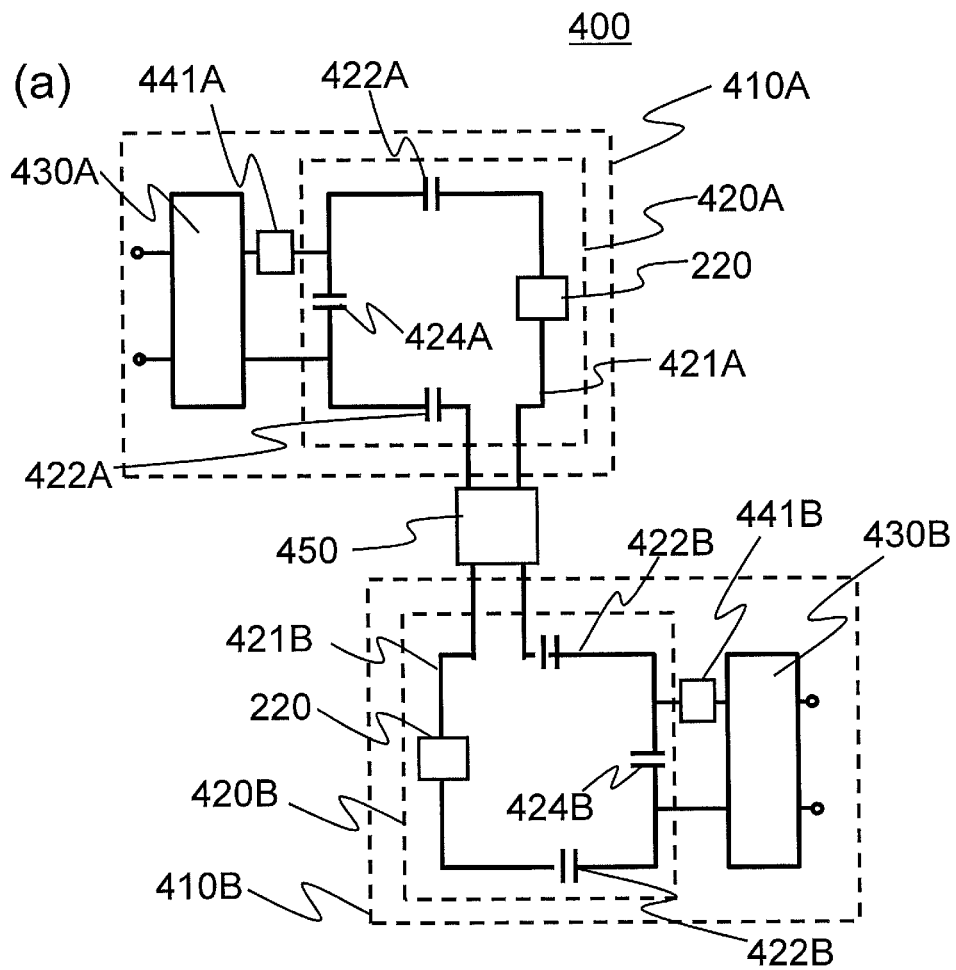
FIG. 5(a) illustrates an embodiment of an array coil used as the receiver RF coil.
FIGS. 5(b) and 5(c) illustrate examples of the transmit-receive magnetic coupling prevention circuit of the receiver RF coil.
Figure 5:
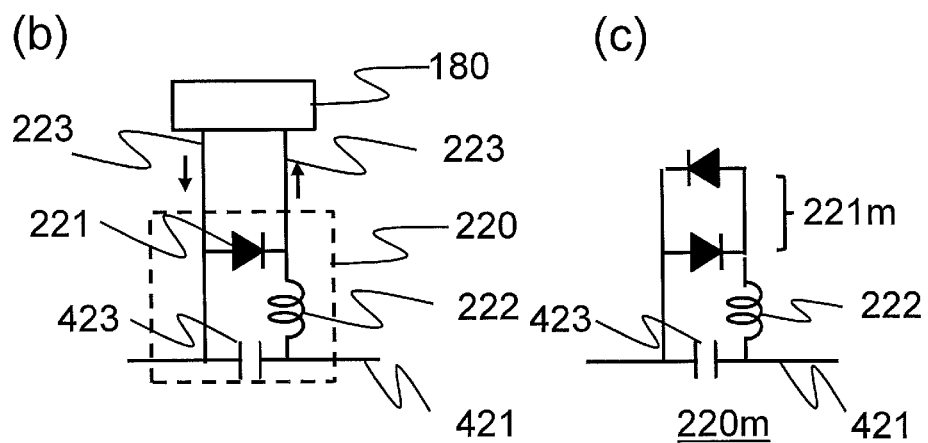

FIG. 5(*a*) illustrates as an example, one transmit-receive magnetic coupling prevention circuit 220 is inserted into the subcoil 410, but the number of the transmit-receive magnetic coupling prevention circuits 220 to be inserted into the subcoil 410 is not limited to one. Two or more transmit-receive magnetic coupling prevention circuits may be inserted into each of the loops 421. By inserting a plurality of the transmit-receive magnetic coupling prevention circuits, the magnetic coupling between the transmit RF coil 151 and the receiver RF coil 161 can be lowered to a sufficient level.

The configuration of the transmit-receive magnetic coupling prevention circuit 220 is not limited to the above-mentioned configuration. As illustrated by a modification example of the transmit-receive magnetic coupling prevention circuit 220*m* in FIG. 5(*c*), a cross diode 221*m* may be employed instead of the PIN diode 221. With this configuration, when large signals pass through the conductor constituting the loop 421, the cross diode 221*m* is turned on, and the capacitor 423 of the loop 421 and the inductor 222 realize parallel resonance at the frequency of the received nuclear magnetic resonance signals, and then high impedance occurs. In this case, the magnetic coupling prevention circuit driver 180 is not necessary.

In the array coil 400 of the present embodiment, values of the inductance and capacitance of the circuit components for adjustment included in each of the subcoils 410A and 410B, and values of the inductance and capacitance provided by the electromagnetic coupler 450 are adjusted, whereby each of the subcoils 410A and 410B is adjusted so that they can receive the nuclear magnetic resonance signals, and the electric fields generated between the subcoils intensify each other, according to the current passing through each coil upon receipt of signals by the subcoils.

Specifically, the first subcoil 410A is arranged in a manner that, upon receipt of signals, the first current (induced current) based on the signals detected by first subcoil 410A passes therethrough, and a part of the first current (the first sub-current) passes through the second subcoil 410B, in the opposite direction of the current in the first subcoil, thereby intentionally guiding the current to flow in the other coil loop unit. Simultaneously, the second subcoil is arranged in a manner that, upon receipt of signals, the second current (induced current) based on the signals detected by the second subcoil 410B passes therethrough, and a part of the second current (the second sub-current) passes through the first subcoil 410A, in the opposite direction of the current in the second subcoil, thereby intentionally guiding the current to flow in the other coil loop unit.

Specific examples of the adjustment method and electromagnetic coupling means will be described in the following embodiments of the RF coil. There will now be described that when induced current passes through one subcoil, a part of the induced current passing through the subcoil also passes through the other subcoil in the form of sub-current, and thereby noise is reduced.

Noise generated from each channel of the receiver RF coil in the MRI apparatus is mainly thermal noise, caused by the subject, and it is Gauss type noise detected by electric field coupling between the coils and subject. This type of noise is increased according to the number of channels, when the channels are combined in reconstructing an image. Furthermore, in the array coil, multiple subcoils are placed adjacent to each other, covering the subject, and thus electric field distributions of the subcoils are likely to be analogous to each other. Accordingly, correlation may occur between the detected signals (noise signals). If this correlation (noise correlation) is strong, noise is intensified upon combining images, and an SNR of the composite image is lowered due to the thus intensified noise. Therefore, it is preferable that the noise correlation should be lower. The noise correlation Ψ between the RF coils is obtained according to the following formulas 1 and 2:

$$R_{ij} = \sigma \int_V \vec{E}_i(x, y, z) \cdot \vec{E}_j^*(x, y, z) dV \tag{1}$$

$$\Psi_{ij} = \frac{R_{ij}}{\sqrt{R_{ii}^* R_{jj}}} \tag{2}$$

where σ is electric conductivity of the subject, V is volume of the subject, Ei is the electric field (complex number) generated by the i-th coil, Ej is the electric field (complex number) generated by the j-th coil. E* represents complex conjugate of E. In other words, the magnitude of noise correlation is determined by volume integral of an inner product of the electric fields that are generated, respectively by the coils within the subject. By reducing the inner product Rij of the electric fields, the noise correlation can be controlled to be low, thereby preventing deterioration of the SNR due to the noise correlation.

Figure 6:
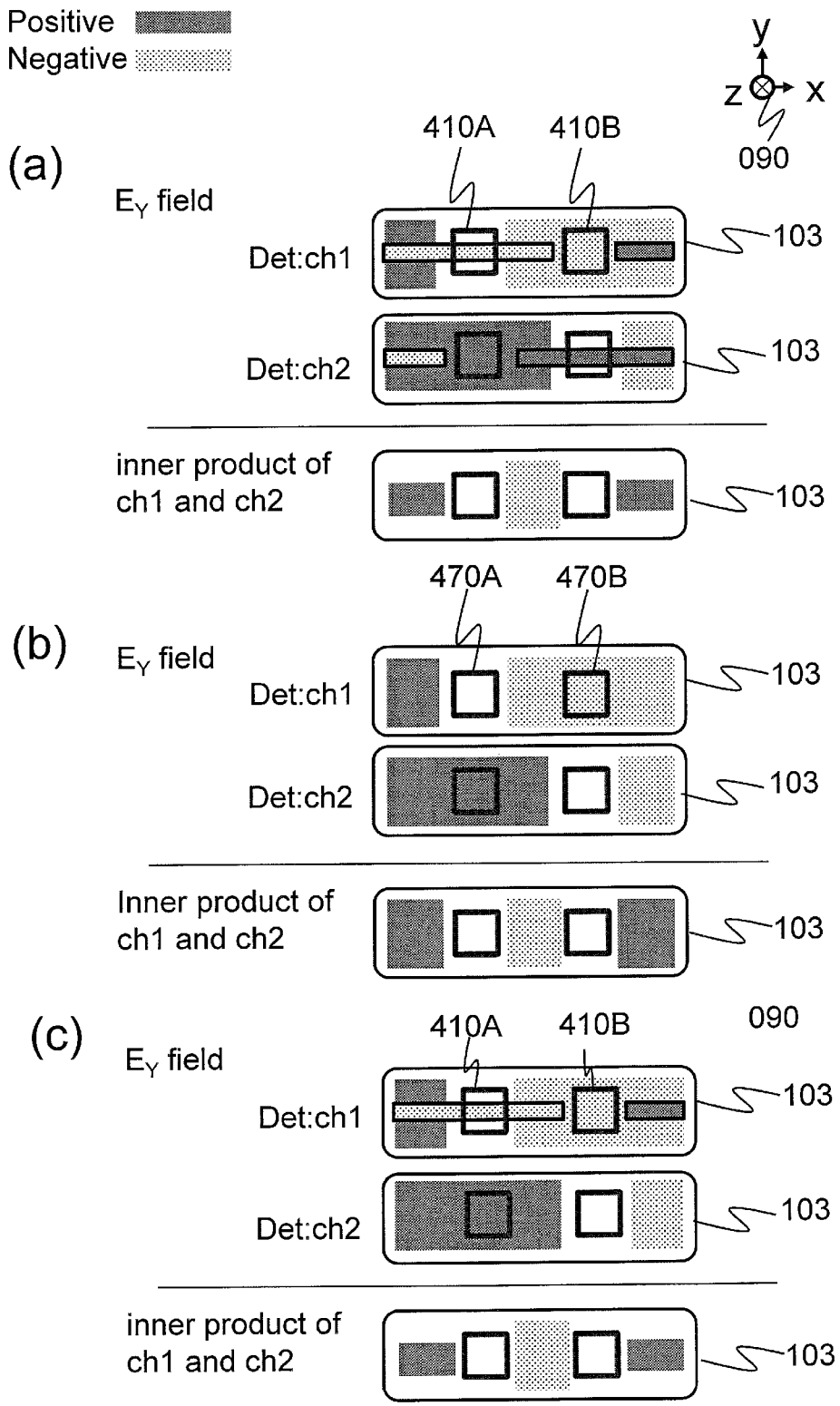
FIGS. 6(a) to 6(c) each illustrates actions and operations of the array coil, according to the present embodiment and a conventional example.

With reference to FIG. 6, there will be described the electric fields that are generated when induced current passes through each of the first subcoil 410A and the second subcoil 410B in the array coil 400 of the present embodiment. In this figure, as one example, the electric field in the y-axis direction is shown, but the electric fields in other axes may also be considered in the same manner.

FIG. 6(*b*) schematically illustrates an electric field distribution that is generated in the subject 103, when clockwise current passes through the subcoils 470A and 470B in the array coil that is provided with a conventional magnetic coupling elimination means. A fine dot pattern indicates a positive electric field, and a coarse dot pattern indicates a negative electric field (the same is applied to FIG. 6(*a*)). In the conventional array coil, when the clockwise current passes through the subcoil 470A, the electric field distribution (Det: ch1) becomes positive on the right side of the subcoil 470A in the figure, whereas in the left side of the figure, the electric field distribution becomes negative. When the clockwise current passes through the subcoil 470B (Det: ch2), the electric field distribution becomes positive on the right side of the subcoil 470B in the figure, whereas in the left side of the figure, the electric field distribution becomes negative. Upon receiving signals by the array coil, the electric field distributions according to those two channels are generated simultaneously. At this time, when the inner product of the electric fields generated in each of the coils is obtained, as shown in the lower row of FIG. 6(b), the electric field becomes negative between the two subcoils 470A and 470B, whereas it becomes positive on both sides.

On the other hand, in the array coil according to the present embodiment, as shown in FIG. 6(a), when clockwise current passes through the subcoil 410A, the electric field distribution in the (Det: ch1) is generated by a part of the current (sub-current) passing though the subcoil 410B, in addition to the electric field generated by the induced current (the first current) passing through the subcoil 410A. In FIG. 6(a), a region surrounded by a narrow rectangular indicates the electric field based on this sub-current. Similarly, when the clockwise current passes through the subcoil 410B, the electric field distribution in the (Det: ch2) includes the electric field according to the induced current passing through the subcoil 410B and the electric field according to the sub-current (a part of the induced current) passing through the subcoil 410A. Consequently, as shown in the lower row of FIG. 6(a), the inner product of the electric fields becomes negative between the two subcoils 410A and 410B, whereas it becomes positive on both sides, but smaller relative to FIG. 6(b).

In other words, in the array coil of the present embodiment, a part of the current (sub-current) passing through one subcoil flows in the opposite direction in the other subcoil. Therefore, the electric fields generated between the subcoils have the same sign and thus they intensify each other, whereas the electric fields generated in the regions other than the region above have different signs and thus they weaken each other. With this configuration, the noise correlation between the coils is reduced, and the SNR of the image obtained by combining channels may be improved.

When a part of the current passing through one subcoil flows into the other subcoil, the current flows in mutually opposite directions, and thus the current flows in so-called figure-of-eight path. However, the current path is not limited to this shape. By way of example, a part of the figure-of-eight path may be cut off. It is only required to establish a current configuration where the electric fields generated in a living body by the current passing through the subcoils, intensify each other between the subcoils. This configuration enhances flexibility in design, and sensitivity can be improved in the area of interest.

Adjustment for generating the part of current (sub-current) in the other subcoil may be performed either in a symmetrical manner or in an unsymmetrical manner. In other words, following adjustments are also applicable; when current flows according to the signals detected by the first subcoil, a part of the current (sub-current) flows into the second subcoil. On the other hand, when current flows according to the signals detected by the second subcoil, no current may pass through the first subcoil, or the amount of current passing through the first subcoil may be different from the amount of the sub-current passing through the second subcoil. FIG. 5 illustrates an example of the array coil comprising two subcoils, but it is further possible to configure such that the array coil comprises three channels or more, and following adjustments are also applicable; at least one subcoil, and two subcoils placed on both sides thereof are provided, and when current passes through the one subcoil, a part of the current passes through the subcoils on both sides, or the part of the current passes through either one of the subcoils on both sides.

Figure 7:
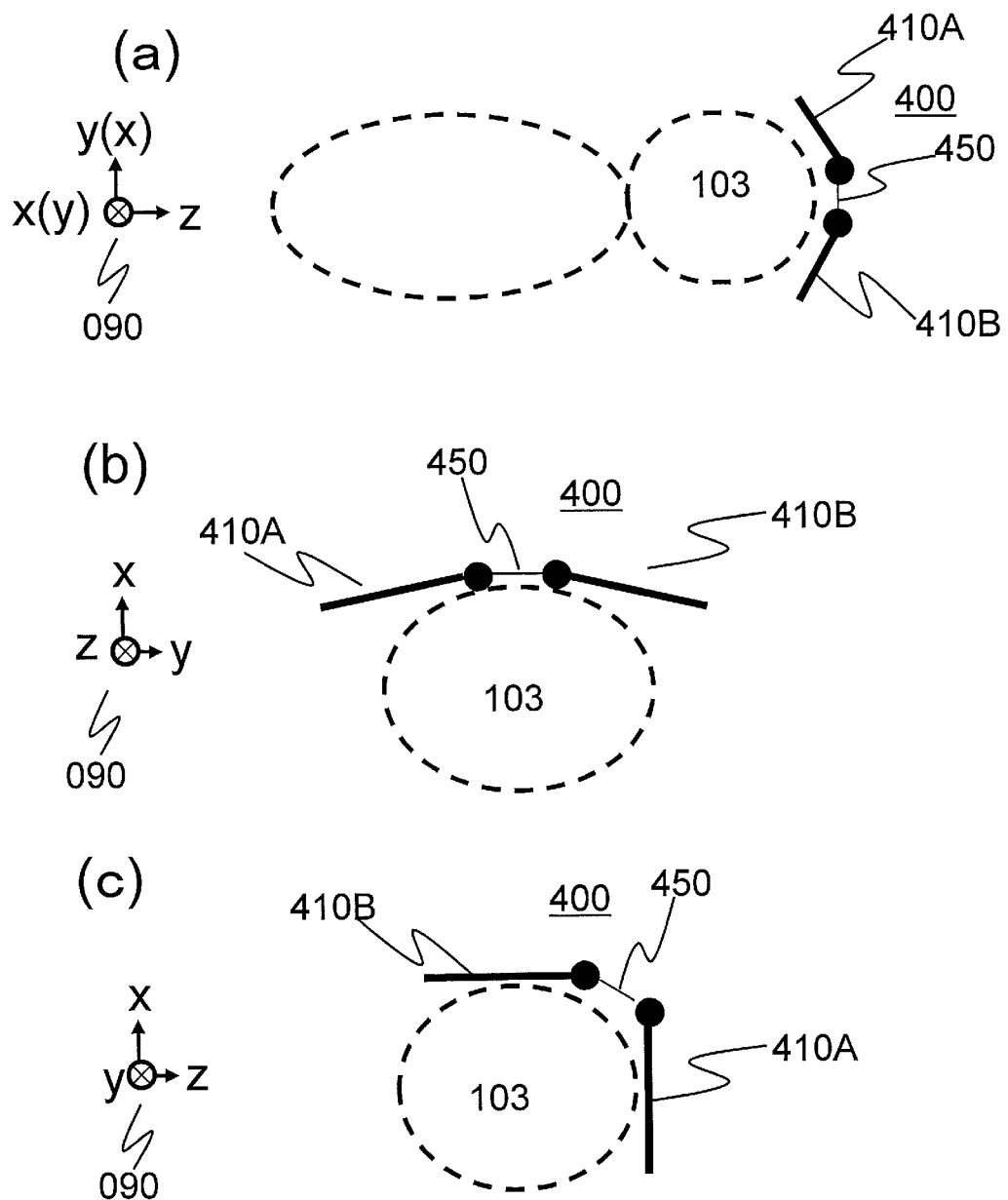
FIGS. 7(a) to 7(c) each illustrates a layout of the array coil in the MRI apparatus of horizontal magnetic field system.

Next, FIG. 7 illustrates a layout example of the array coil 400 of the MRI apparatus according to the present embodiment. FIG. 7(a) illustrates an example that the array coil 400 comprising two subcoils 410A and 410B is arranged on a plane approximately vertical to the direction of the static magnetic field (Z direction), and the subcoils are arranged in the Y-direction. Furthermore as shown in FIG. 7(b), the array coil 400 may be arranged on a plane at an angle approximately parallel to the direction of static magnetic field. Alternatively, as shown in FIG. 7(c), the first subcoil 410A may be arranged on the plane vertical to the static magnetic field, and the second subcoil 410B may be arranged on the plane parallel to the static magnetic field. In addition, even when the array coil is placed on the plane as illustrated in FIG. 7(a) or 7(b), the array of the subcoils may be oriented in the X-direction. Such modification of the layout angle enables detection or generation of rotating magnetic field that cannot be provided by the subcoil 410 alone, allowing acquisition of magnetic resonance signals with high sensitivity in the area of interest.

In the examples as shown in FIGS. 7(a) to 7(c), with regard to the distance between the subcoils (the centers of the loop units) and the body axis of the subject 103, it is preferable that the distance from the two subcoils 410A and 410B should be almost equal, in the viewpoint of reduction of noise correlation. As shown in FIG. 7(b), when the subject 103 has an approximately symmetrical shape with respect to the x-axis, it is preferable that the subcoils should also be arranged symmetrically with respect to the X-axis. With this configuration, the subject-form dependence of the coil properties may be reduced. It should be noted that the symmetry axis is not limited to the X-axis. Any axis (direction) having a property of symmetry with respect to the subject may be applicable.

A configuration of the MRI apparatus of the present embodiment has been described so far. An imaging method using the MRI apparatus of the present embodiment is similar to operations of conventional MRI apparatuses. For example, according to a pulse sequence selected by the imaging method, RF magnetic field pulses are applied from the transmit RF coil 151 (e.g., the birdcage RF coil 300) to the subject 103 that is placed in the static magnetic field space generated by the magnetostatic field magnet 110, together with applying gradient magnetic field pulses from the gradient magnetic field coil 131. During the operation of the transmit RF coil 151, the transmit-receive magnetic coupling prevention circuit 220 is open in the receiver RF coil 161, to remove magnetic coupling with the receiver RF coil 161. After a lapse of a predetermined period from the time the RF magnetic field pulses are applied, the receiver RF coil 161 (multichannel coil: array coil 400) arranged in proximity to the subject 103 receives nuclear magnetic resonance signals that are generated from nuclei of elements constituting living tissues of the subject 103. During the receiving operation, the transmit-receive magnetic coupling prevention circuit 210 becomes open, so as to remove the magnetic coupling between the transmit RF coil 151 and the receiver RF coil 161.

The computer (signal processor) 170 processes MR signals received respectively by the subcoils of the receiver RF coil 161, and if the imaging method thereof is a high-speed imaging method, such as employing a parallel imaging, for example, the computer creates an image of the subject according to the imaging reconstruction method that follows an algorithm of the parallel imaging. It is also possible to obtain an image by subjecting the signals obtained from respective channels to MAC (multi-array coil) synthesis. In creating the image, sensitivity distribution information of each of the subcoils is utilized as appropriate.

According to the MRI apparatus of the present embodiment, a multichannel coil having been adjusted in a particular manner is used as the receiver RF coil, whereby noise correlation between the subcoils is reduced, and a high quality image can be obtained.

In other words, the MRI apparatus of the present embodiment comprises the static magnetic field former configured to form a static magnetic field, the gradient magnetic field former configured to form a gradient magnetic field, the transmit RF coil configured to irradiate a subject placed in the static magnetic field, with an RF magnetic field, the receiver RF coil configured to detect nuclear magnetic resonance signals from the subject, and the signal processor configured to process the nuclear magnetic resonance signals detected by the receiver RF coil.

The receiver RF coil comprises a first subsoil having a first loop coil unit made of a conductor, being capable of receiving nuclear magnetic resonance signals from the subject, a second subsoil having a second loop coil unit made of a conductor, being capable of receiving nuclear magnetic resonance signals from the subject, and an electromagnetic coupler placed between the first subcoil and the second subcoil, for coupling the first subcoil and the second subcoil electromagnetically, wherein adjustments are made in a manner that a part of the first current passing through the first loop coil unit according to signals detected by the first loop coil unit, is made to flow into the second loop coil unit in the form of the first sub-current, and an electric field generated in the subject by the first current and an electric field generated in the subject by the first sub-current intensify each other in the space between the first loop coil unit and the second loop coil unit.

Specifically, at least one of the first subcoil and the second subcoil further comprises a magnetic coupling adjuster connecting the loop coil unit of the subcoil with a low-impedance signal processing circuit that is connected to the subcoil, wherein the magnetic coupling adjuster further comprises at least either of a capacitor and an inductor as an adjusting circuit component, and the loop coil unit comprises a series capacitor that is inserted in series with an inductor component thereof, and a parallel capacitor inserted in series with the inductor component to render the loop coil unit to serve as a parallel resonant circuit, and adjustment of at least one of the subcoils is performed by adjusting values of the adjusting circuit component, the series capacitor, and the parallel capacitor.

The array coil 400 of the present embodiment, which is arranged and adjusted as described above, is tuned to the magnetic resonance frequency f0. Upon signal reception, signals detected by the first loop coil unit 420A pass through the second subcoil 410B, thus forming current that flows in a figure-of-eight path, and the electric fields generated between the loops intensify each other. With this configuration, noise correlation between the first subcoil 410A and the second subcoil 410B is lowered, and accordingly, the SNR of a composite image can be increased.

As discussed so far, according to the array coil 400 of the present embodiment, low noise can be achieved in the form of multichannel. In addition, adjustments of the arrangement and values of the circuit components enable implementation of such multichannel and low noise. Therefore, this may prevent increase in complexity of the configuration. Furthermore, by using this array coil 400 as the receiver RF coil 161, the MRI apparatus of the present embodiment is allowed to obtain a high-quality image targeted to a wide region.

The MRI apparatus of the present invention features in using the receiver RF coil, particularly adjusted, and the configuration other than this feature may be modified variously. By way of example, in the present embodiment some of the components that are shown in FIG. 2 may be excluded, or any component not shown in FIG. 2 may be added. Furthermore, in the aforementioned embodiment, descriptions have been made for the MRI apparatus of the horizontal magnetic field system, but the present embodiment may also be applicable to the MRI apparatus of the vertical magnetic field system.

Figure 8:
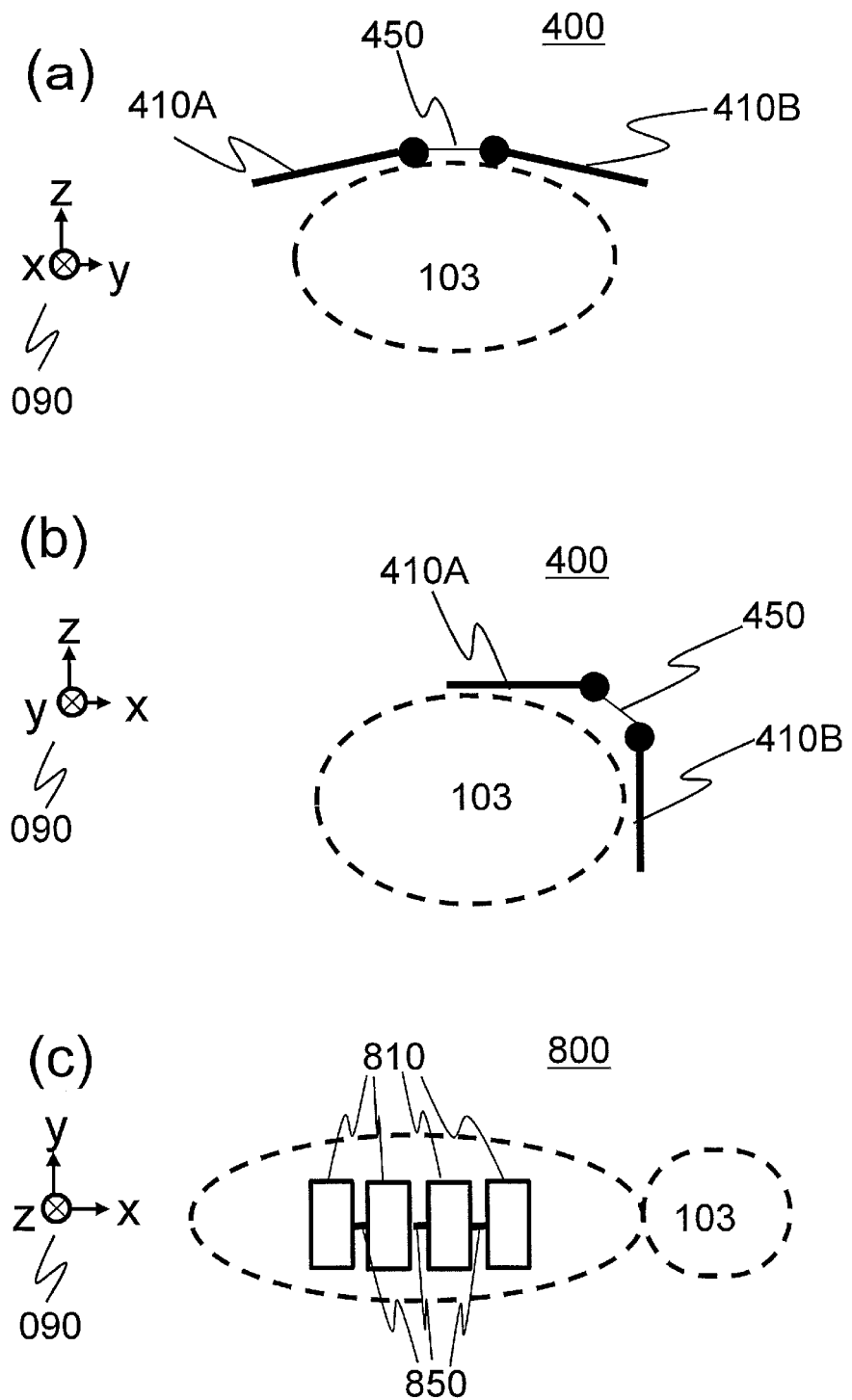
FIGS. 8(a) to 8(c) each illustrates a layout of the array coil in the MRI apparatus of vertical magnetic field system.

FIG. 8 illustrates an arrangement example where the multichannel array coil is employed in the MRI apparatus 101 of the vertical magnetic field system. FIG. 8(a) illustrates an example where two subcoils 410 constituting the array coil 400 are arranged on a plane approximately vertical to the direction of the static magnetic field, and FIG. 8(b) illustrates an example where one of the subcoils is placed on the plane vertical to the direction of the static magnetic field, and the other subcoil is placed on a plane parallel to the direction of the static magnetic field. FIG. 8(c) illustrates an example where a multichannel array coil 800 using multiple surface coils 810 is placed. In the MRI apparatus of the vertical magnetic field system, when the RF coil is placed on the XY plane, a positional relation of the RF coil to the magnetic field direction is vertical. Usually, this relationship makes it hard to efficiently acquire revolving field signals generated on the XY plane, and a ratio of noise is likely to be larger. Therefore conventionally, array coils have not been employed, because the ratio of noise increase has been still large, even though the coil placed on the XY plane is configured to have multichannel. However, noise can be reduced according to the present embodiment, and thus also in the MRI apparatus of the vertical magnetic field system, flexibility in designing the array coil can be enhanced, allowing the sensitivity to be improved. Such enhanced flexibility enables simplification of the array coil, and accordingly, it is further possible to design a lightweight array coil. This may take the load off both an operator and an examinee.

<Embodiments of RF Coil>

Embodiments of the RF coil according to the present invention will now be described. The RF coil of the present invention is a multichannel RF coil that is used as the receiver RF coil of the MRI apparatus, and it is provided with multiple subcoils. Each of the multiple subcoils is capable of receiving nuclear magnetic resonance signals generated in the MRI apparatus, and those subcoils are adjusted so that electric fields generated within the subject by the current passing through each of the subcoils intensify each other between adjacent subcoils. There will be described embodiments of a specific configuration of the coil and an adjusting method for implementing such adjustments as described above.

The array coil (FIG. 5) used as the receiver RF coil as described in the foregoing embodiment of the MRI apparatus is one of the embodiments of the RF coil according to the present invention. Operations (FIG. 6) and modification examples as described in the foregoing embodiment may be commonly applied to each of the following embodiments described below.

First Embodiment

The RF coil of the present embodiment has a configuration similar to the configuration of the array coil 400 as shown in FIG. 5, comprising two subcoils; the first subcoil 410A and the second subcoil 410B, and further comprising an electromagnetic coupler 450 between the subcoils 410A and 410B. The RF coil is adjusted in a manner that a part of the current (sub-current) detected by the first subcoil 410A passes through the second subcoil 410B upon receipt of signals by the first subcoil 410A, and simultaneously, a part of the current (sub-current) detected by the second subcoil 410B passes through the first subcoil 410A upon receipt of signals by the second subcoil 410B. The amount of the sub-current can be adjusted by circuit components provided for the adjustment, being inserted in or connected with the subcoil. The sub-current preferably corresponds to 5% to 30% of the current that is detected by the first subcoil or the second subcoil. With this configuration, the electric fields generated within the subject between the subcoils intensify each other, whereas the electric fields in an area other than this region are weakened, and accordingly, noise correlation can be reduced effectively.

The first subcoil 410A and the second subcoil 410B may be placed approximately on the same plane. Here, "approximately on the same plane" indicates a relationship that adjacent coil elements are placed approximately on the same plane, and a region other than the coil elements (end portions other than the coil elements) may be bent or curved. It is also possible that the first subcoil 410A and the second subcoil 410B are placed in a manner that the coil elements partially overlap one on another.

Figure 9:
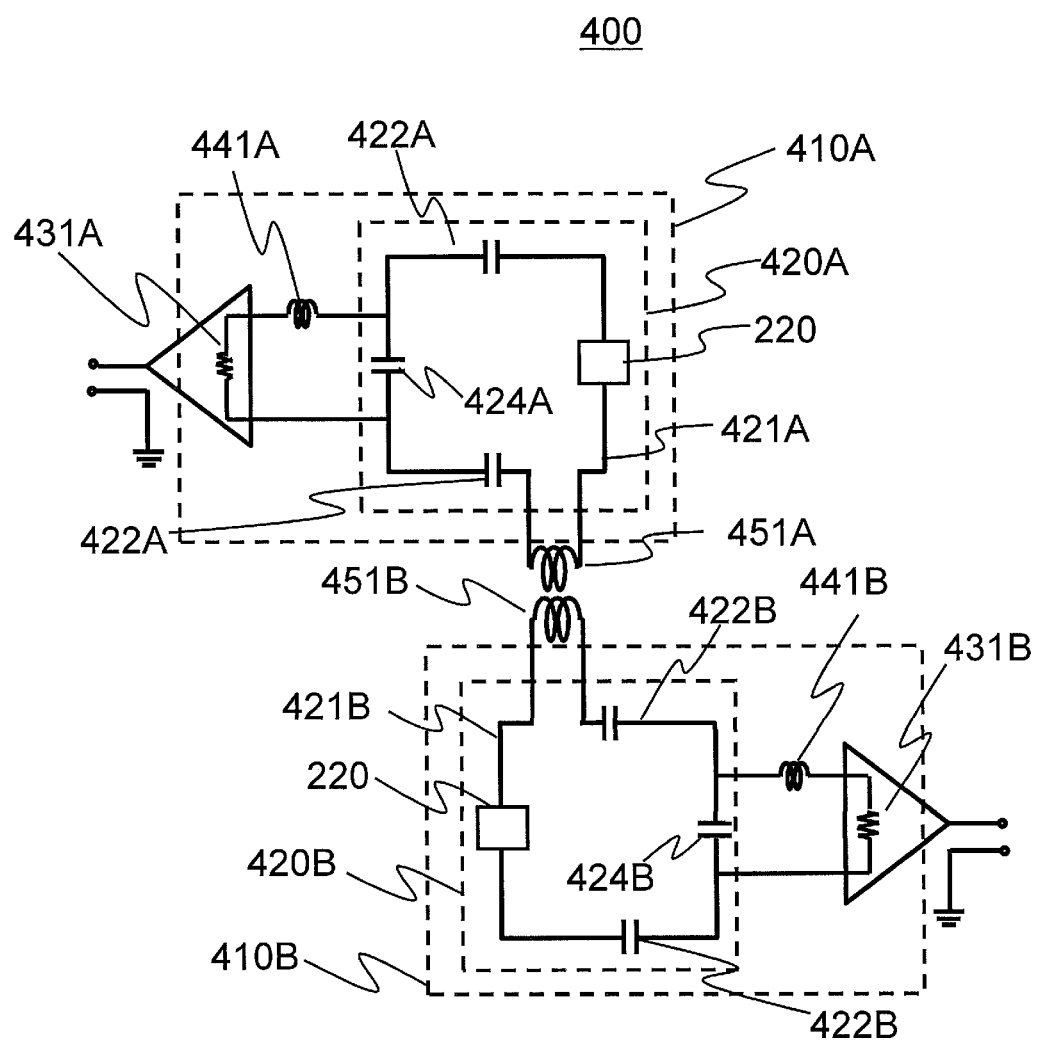
FIG. 9 schematically illustrates the array coil according to a first embodiment.

With reference to FIG. 9, the RF coil of the present embodiment will be described in detail. In FIG. 9, the vertical direction on the figure represents X-axis direction, the horizontal direction on the figure represents Y-axis direction, and the direction orthogonal to the paper plane represents Z-axis direction. Also in the present embodiment, if there is no need to particularly identify components of each of the subcoils 410, where the subcoils 410 constitute the array coil 400, the alphabets attached to the end of the reference numerals may be omitted.

As shown in FIG. 9, in the present embodiment, there will be described an example where the first subcoil 410A and the second subcoil 410B are placed in a manner that a plane formed by the loop 421 of the loop coil unit 420 in each subcoil becomes relatively close to a plane that is vertical to the magnetic field direction (Z axis direction). It is to be noted that the loop 421 of the loop coil unit 420 may have any shape, such as the rectangle as illustrated, a polygonal, and a circular shape (including an oval shape).

In the present embodiment, the electromagnetic coupler 450 between the two subcoils 410A and 410B includes an inductor 451A on the first subcoil 410A side and an inductor 451B on the second subcoil 410B side, and the two subcoils 410A and 410B are coupled according to magnetic coupling.

The array coil of the present embodiment employs low-input impedance signal amplifiers 431A and 431B, respectively as the first low-impedance signal processing circuit 430A and the second low-impedance signal processing circuit 430B. By using the low-input impedance signal amplifier 431, signals detected by the loop coil unit 420 can be amplified immediately, and thus data with less noise can be acquired. A magnitude of input impedance of the low-input impedance signal amplifier 431 is not limited, but it may be approximately equal to or less than $2\Omega$. It should be noted that the low-impedance signal processing circuit 430 is not restricted to the low-impedance signal amplifier 431.

The series capacitors 422, the transmit-receive magnetic coupling prevention circuit 220 (including the capacitor 423), and the parallel capacitor 424, which are inserted in each loop coil unit 420, are configured the same as those in the array coil illustrated in FIG. 5. Also in the present embodiment, three capacitors (such as 422 and 424) are inserted in the loop 421 of the loop coil unit 420, but the number of the capacitors is not limited to this example. It is sufficient if at least one capacitor is inserted.

Further in the embodiment as shown in FIG. 9, an inductor (referred to as an adjustment inductor, for the purpose of distinguishing from other inductors) is used as the electromagnetic coupling adjuster 441, but the inductor is not necessarily used as the electromagnetic coupling adjuster 441. Generally, the parallel capacitor 424 is connected to the electromagnetic coupling adjuster 441 via a conductor. Since the conductor contains an inductor component, even without additional inductor, the parallel capacitor 424, the electromagnetic coupling adjuster 441, and the inductor component contained in the conductor connecting therebetween may form a parallel resonant circuit. If a resonance frequency of this parallel resonant circuit can be adjusted according to any method, a capacitor may also serve as the electromagnetic coupling adjuster 441. Alternatively, a parallel circuit of the capacitor and the inductor may also serve as the electromagnetic coupling adjuster 441. For ease of explanation, there shall be no inductor component contained in the conductor for connecting the parallel capacitor 424 with the electromagnetic coupling adjuster 441, in the following description.

Next, each of the circuit components in the array coil 400 of the present embodiment will be described. Assuming that the transmit RF coil 151 is constantly in the open state, removal of the magnetic coupling between the transmit RF coil 151 and the receiver RF coil 161 shall not be described in this example.

The first subcoil 410A and the second subcoil 410B of the array coil 400 according to the present embodiment implement the aforementioned functions, by adjusting values of the inductor 451A and the inductor 451B constituting the electromagnetic coupler 450, the first electromagnetic coupling adjuster 441A, the second electromagnetic coupling adjuster 441B, the first series capacitors 422A, the second series capacitors 422B, the first parallel capacitor 424A, and the second parallel capacitor 424B.

Figure 10:
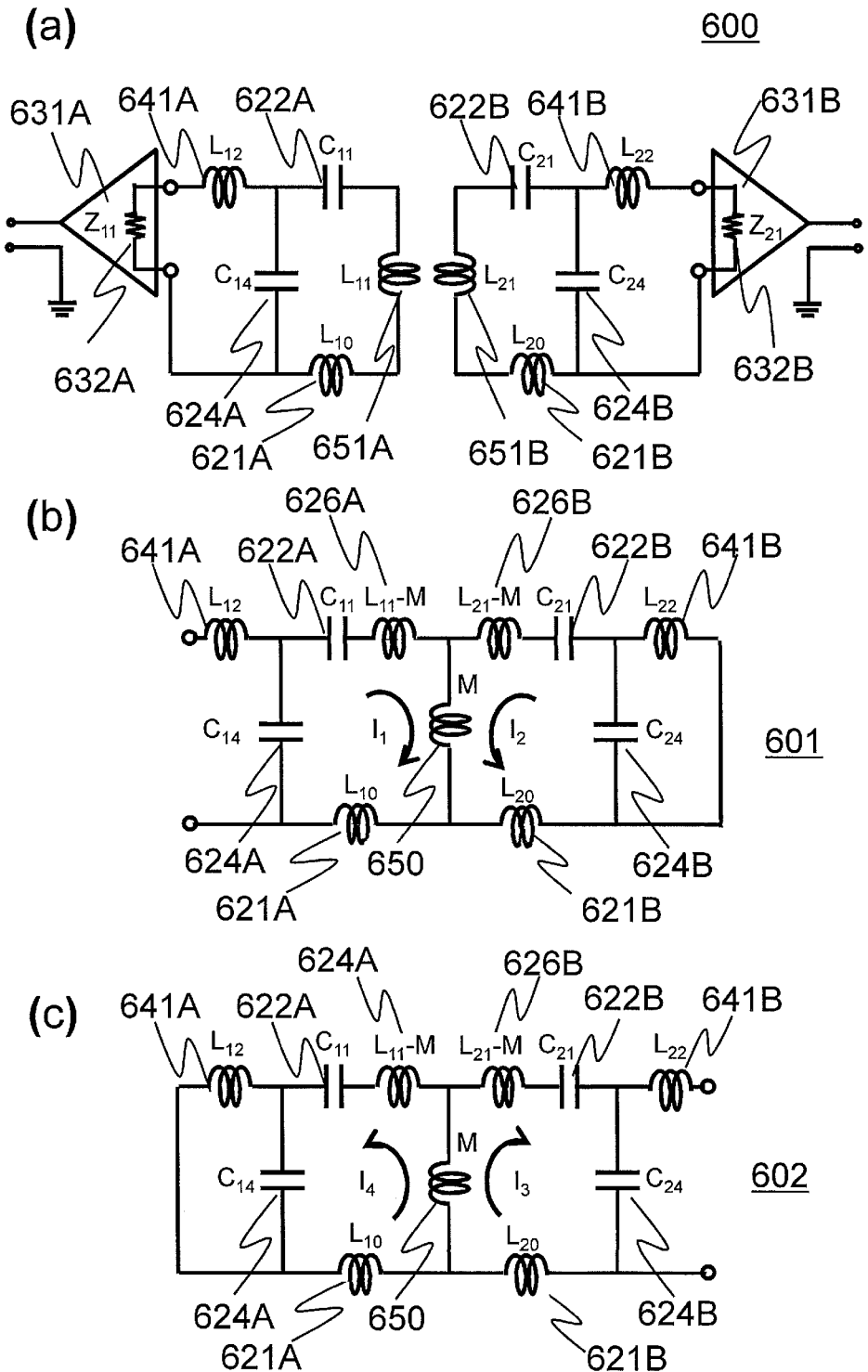
FIG. 10(a) illustrates an equivalent circuit of the array coil according to the first embodiment.
FIG. 10(b) illustrates the equivalent circuit looked at a low-impedance circuit side of the first subcoil side.
FIG. 10(c) illustrates the equivalent circuit looked at the low-impedance circuit side of the second subcoil side.

Adjustment of each of those circuit components will be described with reference to equivalent circuits of the array coil 400 as illustrated in FIG. 10. FIG. 10(a) illustrates the equivalent circuit 600 of the array coil 400 according to the present embodiment. The number value in the hundreds digit of the reference numeral representing each component as shown in FIG. 9 is altered from "4" to "6", to indicate the corresponding component in FIG. 10. By way of example, the inductor is 641 in FIG. 10 corresponds to the inductor 441 in FIG. 9, and the series capacitor 622 in FIG. 10 corresponds to the capacitor 422 in FIG. 9. The capacitor 622A corresponds to a combination of two of the first series capacitors 422A, and the capacitor 622B corresponds to a combination of two of the second series capacitors 422B. The inductor 621A indicates the inductor component of the first loop 421A, and the inductor 621B indicates the inductor component of the second loop 421B. Furthermore, values of the inductors and the capacitors being the components, are represented by the reference symbols L and C, respectively, each with a subscript, shown in proximity to the respective components.

The value Z11 of the impedance 632A corresponds to a value of the input impedance of the low-input impedance signal amplifier 431A used as the first low-impedance signal processing circuit 430A. The value Z21 of the impedance 632B corresponds to a value of the input impedance of the low-input impedance signal amplifier 431B used as the second low-impedance signal processing circuit 430B. Those impedance values Z11 and Z21 are sufficiently low, and therefore, they shall be considered as 0Ω (short circuits) in the following.

FIGS. 10(b) and 10(c) illustrate the equivalent circuits showing the state that the first subcoil and the second subcoil as shown in FIG. 10(a) are coupled via the electromagnetic coupler 450. The equivalent circuit 601 as shown in FIG. 10(b) indicates the equivalent circuit of the first subcoil 410A (the first resonator), excluding the low-impedance signal processing circuit 430A (631A), in the state where the current of the first loop coil unit 420A passes through the second loop coil unit 420B, when looked at the first low-impedance signal processing circuit 430A (631A). The equivalent circuit 602 as shown in FIG. 10(c) indicates the equivalent circuit of the second subcoil 410B (the second resonator), excluding the low-impedance signal processing circuit 430B (631B), in the state where the current of the second loop coil unit 420B passes through the first loop coil unit 420A, when looked at the second low-impedance signal processing circuit 430B (631B).

In those equivalent circuits 601 and 602, the inductor 451A of the electromagnetic coupler 450 for the first loop coil unit 420A, and the inductor 451B of the electromagnetic coupler 450 for the second loop coil unit 420B are collectively referred to as a mutual inductance 650, and M represents a value of the mutual inductance 650. The magnitude of the mutual inductance 650 is expressed by the following formula 3.

$$M = k\sqrt{L_{11}L_{21}} \quad (3)$$

where k is a magnetic coupling coefficient, representing a value that indicates a ratio of coupling between the inductor 451A and the inductor 451B. The magnetic coupling coefficient k is a value between or equal to 0 and 1. L11 indicates the magnitude of the inductor 451A of the first subcoil 410A, and L21 indicates the magnitude of the inductor 451B. In other words, the mutual inductance M is determined by the magnitude of the inductors, and the magnetic coupling coefficient. Variation of the distance between the inductors 451B and 451A enables adjustment of the amount of electromagnetic coupling. Therefore, controlling the magnitude of the inductors and the distance between the subcoils allows adjustment of the amount of the sub-current (a part of the current detected by one subcoil and passing through the other subcoil).

Depending on the arrangement, there may also be mutual inductance according to the inductor component of the first loop coil unit 420A and the inductor component of the second loop coil unit 420B. In the example here, for ease of explanation, all those inductor components shall be included within the mutual inductance between the inductor 451A and the inductor 451B.

Next, there will be described adjustment of the circuit components in the array coil 400 having the aforementioned circuit configuration. A resonance frequency of the series resonant circuit only comprising the parallel capacitor 424A, the adjustment inductor 441A, and the first low-impedance signal processing circuit 430A, is represented by f10. Similarly, a resonance frequency of the series resonant circuit only comprising the parallel capacitor 424B, the adjustment inductor 441B, and the second low-impedance signal processing circuit 430B, is indicated as f20. Further as shown in FIG. 10(b), upon receiving signals, the resonance frequency of the resonator of the first subcoil 410A (the first resonator) is indicated as f11, when looked at the first low-impedance signal processing circuit 430A (631A). As shown in FIG. 10(c), the resonance frequency of the resonator of the second subcoil 410B (the second resonator) is indicated as f21, when looked at the second low-impedance signal processing circuit 430B (631B). In addition, the frequency of the nuclear magnetic resonance signal to be detected (the nuclear magnetic resonance frequency) is indicated as f0.

Each of the circuit components of the array coil 400 according to the present embodiment is adjusted so that each of the aforementioned resonance frequencies satisfies the following formulas 4 to 8.

$$f11 = f21 = f0 \quad (4)$$

$$f10 \neq f0 \quad (5)$$

$$f20 \neq f0 \quad (6)$$

$$\frac{1}{2\pi\sqrt{L_{12}C_{14}}} \neq f_0 \quad (7)$$

$$\frac{1}{2\pi\sqrt{L_{22}C_{24}}} \neq f_0 \quad (8)$$

When each of the circuit components is adjusted according to the formulas 5, 7, both ends of the capacitor 424A of the first subcoil 410A do not become highly resistant upon receiving signals. Therefore, this facilitates flowing of the current from the second subcoil 410B into the first subcoil 410A. Similarly, when each of the circuit components is adjusted according to the formulas 6 and 8, both ends of the capacitor 424B of the second subcoil 410B do not become highly resistant upon receiving signals. Therefore, this facilitates flowing of the current from the first subcoil 410A into the second subcoil 410B.

As shown in FIG. 10(b), according to the adjustment above, upon receiving signals, the first resonator of the first subcoil 410A becomes the circuit 601 where the inductor component (L10) of the first loop 421A and the inductor component (L20) of the second loop 421B allow current to flow via the inductors 451A and 451B of the magnetic coupler 450. In FIG. 10(b), the value of the inductor 626A and the value of the inductor 626B are equal to the values obtained by subtracting the value M of the mutual inductance, respectively from the values L11 and L21 of the inductors 651A (inductor 451A) and 651B (451B).

At this time, as shown in FIG. 10(b), when each of the circuit components is adjusted so that magnetic coupling (a function of the magnetic coupler 450) allows for example, circulating current I1 in a clockwise direction to pass through the first loop 421A, and circulating current I2 in a counterclockwise direction to pass through the second loop 421B, resulting in that a current path having a figure-of-eight shape is formed effectively by the loop 421A and the loop 421B, and current passes therethrough. In addition, by adjusting each of the circuit components according to the formula 4, the coils are tuned to the magnetic resonance signals, and nuclear magnetic resonance signals can be detected.

Similarly, in the circuit 602 as shown in FIG. 10(c), upon receiving signals, the second resonator of the second subcoil 410B becomes the circuit 602 where the inductor component (L20) of the second loop 421B and the inductor component (L10) of the first loop 421A allow current to flow via the inductors 451A and 451B of the magnetic coupler 450.

At this time, as shown in FIG. 10(c), when each of the circuit components is adjusted so that magnetic coupling allows, for example, circulating current I4 in a counterclockwise direction to pass through the first loop 421A, and circulating current I3 in a clockwise direction to pass through the second loop 421B, resulting in that a current path having a figure-of-eight shape is formed effectively by the loop 421A and the loop 421B, and current passes therethrough. In addition, by adjusting each of the circuit components according to the formula 4, the coils are tuned to the magnetic resonance signals, and nuclear magnetic resonance signals can be detected.

According to the adjustment as described above, each of the subcoils 410 is allowed to receive the nuclear magnetic resonance signals from the subject as a detection target. Forming of the current path as described above may generate the electric fields as shown in FIG. 6(a), whereby noise correlation is reduced. Furthermore, in any of the cases above, a part of the current in one coil is made to flow in the other coil, and thus it is possible to provide various sensitivity distributions for a region to be imaged. Therefore, this allows those coils to function as a multichannel coil.

Adjustment Example 1

There will now be specifically described a procedure for adjusting each of the circuit components according to the present embodiment. In the present example, description will be made, taking an example where the array coil 400 is adjusted to resonate at 64 MHz (f0=64 MHz), corresponding to the magnetic resonance frequency of hydrogen nucleus in the static magnetic field strength 1.5 T (tesla).

As for the shape and the size of the subcoil, in an example, the shape of the loop is rectangle, and the diameter of each of the loops 421A and 421B is set to be 100 mm, respectively for the first loop coil unit 420A and the second loop coil unit 420B. In addition, the distance between the centers of the two subcoils 410 is set to be 140 mm.

As shown in FIG. 10(b), when the first subcoil 410A is electromagnetically coupled with the second subcoil 410B, adjustments are made so that current in the clockwise direction passed through the first loop 421A and current in the counterclockwise direction passes through the second loop 421B, so as to form the current path having the figure-of-eight shape effectively by the loop 421A and the loop 421B. Specifically, it is adjusted in a manner that 10% of the current passing through the first loop 421A is made to pass through the second loop 421B.

Simultaneously, as shown in FIG. 10(c), when the second subcoil 410B is electromagnetically coupled with the first subcoil 410A, adjustments are made so that current in the clockwise direction passes through the second loop 421B and current in the counterclockwise direction passes through the first loop 421A, so as to form the current path having the figure-of-eight shape effectively by the loop 421A and the loop 421B. Specifically, it is adjusted in a manner that 10% of the current passing through the second loop 421B is made to pass through the first loop 421A.

For this purpose, firstly, each of the circuit components of the second subcoil 410B is adjusted. Values of the capacitance C21 of the series capacitor 622B and the capacitance C24 of the parallel capacitor 624B are adjusted. Here, those values are adjusted so that the equivalent circuit 602 as shown in FIG. 10(c) could resonate at 64 MHz, and impedance across the series circuit of the adjustment inductor 641B and the parallel capacitor 624B should become 50Ω.

Simultaneously, the value L22 of the adjustment inductor 641B and the value C24 of the parallel capacitor 624B are adjusted so that the formula 8 is satisfied.

At this time, in order to make the current flow upon coupling as described above, the values of L22 and C24 are determined so that the parallel resonant circuit (referred to as L22C24 resonant circuit) made up of the adjustment inductor 641B and the parallel capacitor 624B, could operate as a capacitor. Those values are adjusted on the basis of a principle of the parallel resonant circuit characteristic. The principle of the parallel resonant circuit characteristic will be described later. In the present embodiment, those values are adjusted so that the resonance frequency (f10) of the L22C24 resonant circuit could be a value smaller than f0. By way of example, 51 MHz is used as the value smaller than f0, which is 20% lower.

Next, each of the circuit components in the first subcoil 410A is adjusted. It is assumed that at this stage, the circuit components in the second subcoil 410B have already been adjusted as described above.

In this example, the value C11 of the series capacitor 622A and the value C14 of the parallel capacitor 624A are adjusted so that the equivalent circuit 601 as shown in FIG. 10(b) could resonate at 64 MHz, and the impedance at the both ends of the series circuit of the inductor 641A and the parallel capacitor 624A (C14) should become 50Ω.

Simultaneously, the value L12 of the adjustment inductor 641A and the value C14 of the parallel capacitor 624A are adjusted in a manner that the formula 7 is satisfied, so that the second subcoil 410B could be electromagnetically coupled with the first subcoil 410A. At this time, in order to make the current flow upon coupling as aforementioned, the values of L12 and C14 are determined so that the parallel resonant circuit (L12C14 resonant circuit) made up of the adjustment inductor 641A and the parallel capacitor 624A could operate as a capacitor. Those values are adjusted on the basis of a principle of the parallel resonant circuit characteristic. The principle of the parallel resonant circuit characteristic will be described later. In the present embodiment, those values are adjusted so that the resonance frequency (f20) of the L12C14 resonant circuit could become a value smaller than f0. By way of example, 51 MHz is used as the value smaller than f0, which is 20% lower.

In order to achieve a current ratio of 10%, a coupling amount of electromagnetic coupling is adjusted by varying the distance between the inductors 451B and 451A of the magnetic coupler 450. In this example, the values of both the inductors 451B and 451A are set to 50 nH.

Such adjustments of the first subcoil 410A and the second subcoil 410B may be repeated several times as required.

When 51 MHz is used as the value smaller than f0, the values of the parameters obtained according to the above adjustments, may be as the following, for example; C11=20.2 pF, C14=225 pF, C21=20.2 pF, C24=225 pF, L12=26 nH, and L22=26 nH.

With the adjustments as described above, the array coil 400 of the present embodiment resonates at the frequency of the nuclear magnetic resonance, and receives nuclear magnetic resonance signals. In addition, two subcoils 410A and 410B form the current flow having the figure-of-eight shape. In other words, as shown in the upper part and the middle part of FIG. 6(a), the electric fields generated between the subcoils are adjusted so that they intensify each other. Noise correlation is obtained by the inner product of those electric fields. Therefore, when the inner product is obtained in each region, as shown in the lower part of FIG. 6(a), in the present embodiment, the region between the coils indicates a large negative value relative to the other regions. In other words, since the noise correlation is obtained by the inner product, it indicates a negative value with respect to the conventional method as shown in FIG. 6(b). Consequently, this means that the noise correlation becomes smaller than the conventional method.

Simultaneously in the present embodiment, since the value of the resonance frequency of the L12C14 resonant circuit and that of the L22C24 resonant circuit are lower than f0 by 20%, the L12C14 resonant circuit and the L22C24 resonant circuit are allowed to operate like capacitors, and the first subcoil 410A and the second subcoil 410B operate being tuned to each other. Therefore, the sensitivity region is enlarged with higher sensitivity, and consequently, the SNR of the composite image can be improved.

[Principle of the Parallel Resonant Circuit Characteristic]

Figure 11:
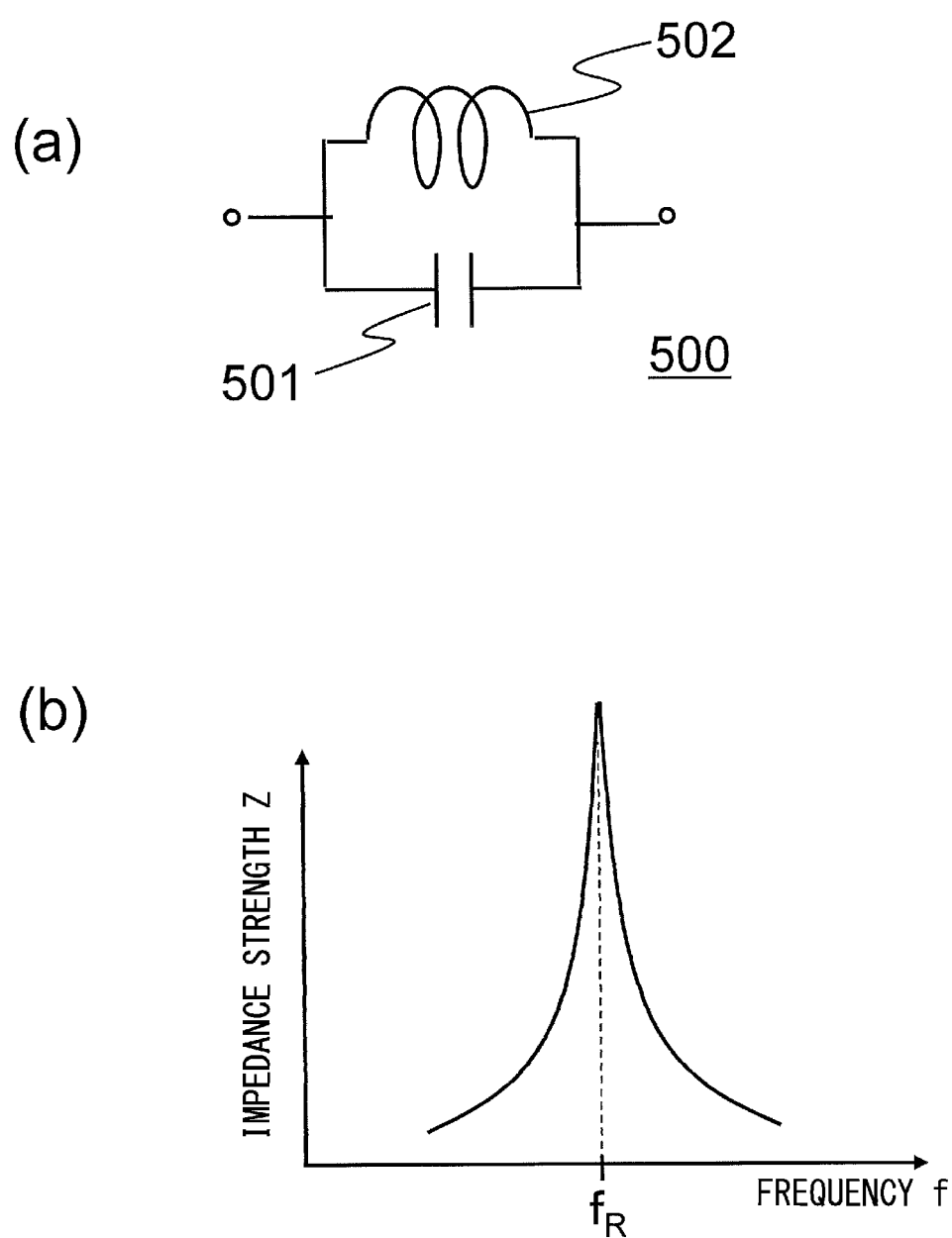
FIGS. 11(a) and 11(b) illustrate operations of a general parallel resonant circuit.

Characteristic of the parallel resonant circuit used in the aforementioned example 1 will be described. FIG. 11(a) and FIG. 11(b) illustrate an operation of the parallel resonant circuit.

As shown in FIG. 11(a), in the parallel resonant circuit 500, the inductor 502(L) and the capacitor 501(C) are connected in parallel. The impedance Z at the both ends of the parallel resonant circuit 500 is expressed by the following formula 9, where the frequency of the voltage applied to the parallel resonant circuit 500 is f, and an angular frequency is ω (ω=2πf).

$$\frac{1}{Z} = j\omega C + \frac{1}{j\omega L} \tag{9}$$

As shown in FIG. 11(b), the impedance Z varies depending on the frequency f being applied, and resonance occurs at a predetermined frequency (referred to as the resonance frequency fR). In other words, the impedance Z at the both ends of the parallel resonant circuit 500 is maximized at the frequency fR.

The impedance Z is expressed by the formula 10 at a frequency lower than the resonance frequency fR of the parallel resonant circuit 500 (f<fR), and the parallel resonant circuit 500 operates as an inductive reactance (inductor).

$$Z = \frac{1 - (f/f_R)^2}{j2\pi fL} \tag{10}$$

Here, the value L' of virtual inductance of the parallel resonant circuit 500 is expressed by the formula 11.

$$L' = \frac{L}{1 - (f/f_R)^2} \tag{11}$$

On the other hand, the impedance Z is expressed by the formula 12 at a frequency higher than the resonance frequency fR of the parallel resonant circuit 500 (f>fR), and the parallel resonant circuit 500 operates as a capacitive reactance (capacitor).

$$Z = j2\pi fC \frac{(f/f_R)^2 - 1}{(f/f_R)^2} \tag{12}$$

Here, the value C' of apparent capacitance of the parallel resonant circuit 500 is expressed by the formula 13.

$$C' = \frac{(f/f_R)^2 - 1}{(f/f_R)^2} C \tag{13}$$

As described above, the parallel resonant circuit 500 operates differently in accordance with the frequency f of the applied voltage, with a boundary of its resonance frequency fR. In the aforementioned example of the adjustments, by using such characteristic of the parallel resonant circuit 500, the value of the resonance frequency, the values of L12 and C14, and the values of L22 and C24 are determined, so that the L12C14 resonant circuit and the L22C24 resonant circuit could operate as the capacitor.

Result of Example 1

Figure 12:
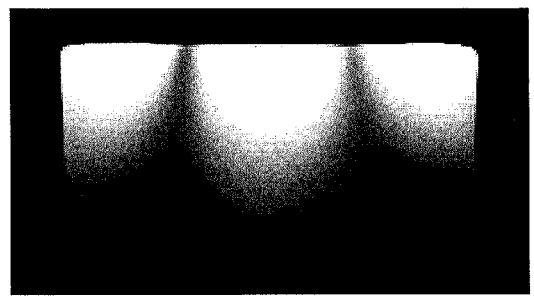
FIG. 12(a) shows a result of imaging by a conventional array coil (comparative example)
FIG. 12(b) shows a result of imaging by the array coil (example 1) according to the first embodiment.
FIG. 12(c) is a graph showing sensitivity profiles of the embodiment and the comparative example.
Figure 12:
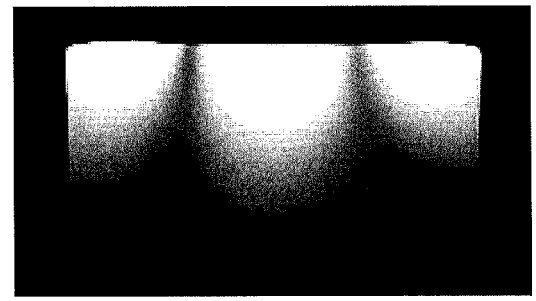
Figure 12:
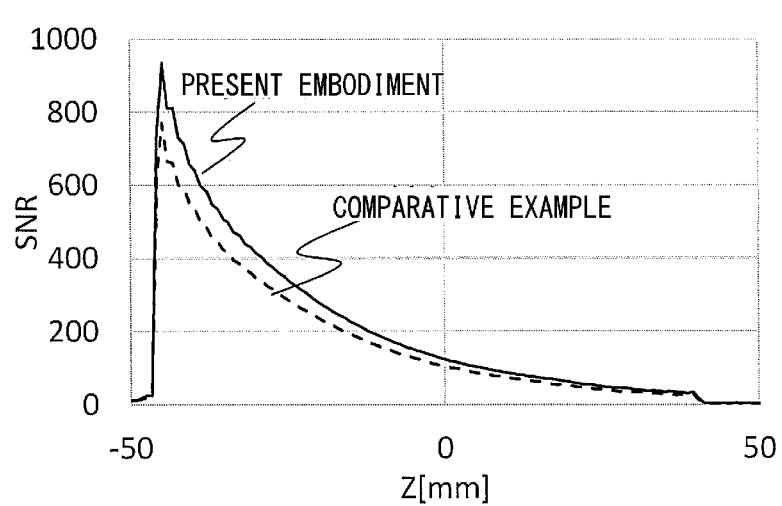

FIG. 12 illustrates simulation results of imaging a water phantom by the MRI apparatus (1.5 tesla, horizontal magnetic field system), using the array coil (the number of subcoils=2) adjusted as described above. FIG. 12(a) shows a result of imaging as a comparative example where a conventional array coil (the number of subcoils=2, and a magnetic coupling remover was provided between the subcoils), and FIG. 12(b) is a result of imaging according to the present embodiment. Noise correlations were 0.15 and 0.01, respectively.

In addition, FIG. 12(c) illustrates a sensitivity profile on the Z-axis after sensitivities of the two subcoils are combined. The solid line indicates the profile of the present embodiment and the broken line indicates the profile of the conventional RF coil (comparative example) where the magnetic coupling has been removed. In the present embodiment, the resonance frequency of the parallel resonant circuit (L22C24 resonant circuit) made up of the adjustment inductor 641B (L22) and the parallel capacitor 624B (C24) was adjusted to 51 MHz, which was smaller value than f0.

As seen from those results, according to the array coil 400 of the present embodiment configuring a current distribution having a shape like figure-of-eight by electromagnetic coupling, the noise correlation was reduced and the SNR of the resultant composite image was improved.

In the present embodiment, both the L12C14 resonant circuit and the L22C24 resonant circuit were set to be the value lower than f0 by 20%, but the value is not limited to this value. It is only required to generate current having the figure-of-eight shape, so as to achieve adjustments for reducing the noise correlation. In addition, the resonance frequency of the L12C14 resonant circuit may be different from the resonance frequency of the L22C24 resonant circuit. Such difference in resonance frequencies may allow deriving of an optimum SNR that is suitable for the shape of the coils. Further in the aforementioned embodiment, 51 MHz was used as a value lower than f0 (64 MHz) for the adjustments of the resonance frequency of the L22C24 resonant circuit, but any other values may be applicable as the resonance frequency of the L22C24 resonant circuit.

Adjustment of this value allows adjustment of a phase difference between the first current passing through the first loop coil unit 420A, and the second current passing through the second loop coil unit 420B. When the current phase difference θ becomes π/2<θ<3π/2, current having the figureof-eight shape can be generated. Basically, it is desirable that the phase difference should be π.

Figure 13:
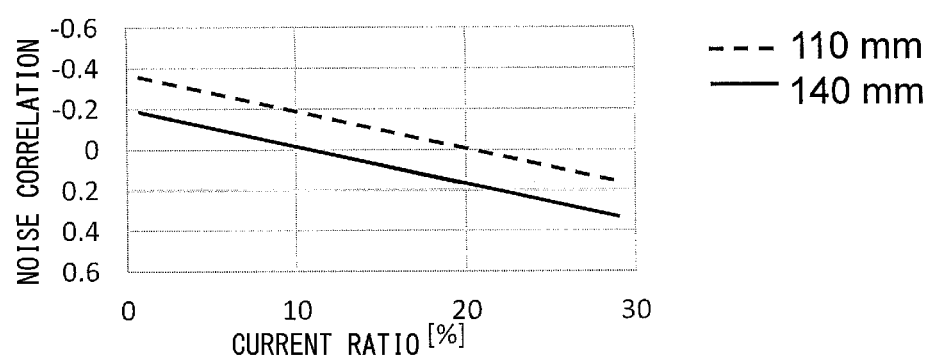
FIG. 13 is a graph showing a relationship between a current ratio of sub-current and noise correlations.

In the present embodiment, the amount of the sub-current (the current ratio) was adjusted to 10%. However, it is essential only that the amount of the sub-current should allow the noise correlation to change to any value enabling enhancement of the SNR in a targeted imaging area, and thus the amount of the sub-current may be adjusted appropriately, in accordance with the distance between coils or other conditions. FIG. 13 is a graph showing the relationship between the noise correlation and the current. The solid line indicates the relationship when the distance between coils (distance between the centers of the loop sections of the subcoils) is 140 mm (Example 1), and the dotted line indicates the relationship when the distance is 110 mm. In the case where the distance between coils is 140 mm, the noise correlation becomes 0.2 according to the conventional method, where the current ratio is adjusted to be 0%. On the other hand, when the current ratio is 10%, the noise correlation becomes zero. In the case where the distance between coils is 110 mm, when the current ratio is 0%, the noise correlation becomes 0.4. On the other hand, by increasing the current ratio, the noise correlation is reduced, and when the current ratio is 20%, the noise correlation becomes zero. As thus described, with the variation of the current ratio in accordance with the position and arrangement of the coils, a desired noise correlation can be achieved. Basically, it is desirable that the amount of the sub-current passing through the other subcoil should fall into the range from 5 to 30% of the current that is detected by one subcoil. In addition, the amount of the first sub-current (sub-current passing through the subcoil 410A) may be equal to or different from that of the second sub-current (sub-current passing through the subcoil 410B). Such difference may allow deriving of an optimum SNR that is suitable for the shape of the coils. Furthermore, since the noise correlation may vary depending on the shape and the size of the subject and the arrangement of coils, it is preferable to define the position and arrangement of coils and to adjust the values, considering the shape of the subject to some extent.

The RF coil (array coil) of the present embodiment is adjusted in a manner that a part of the first current passing through the first loop coil unit according to the signals detected by the first loop coil, flows into the second loop coil unit as the first sub-current, and an electric field generated by the first current within the subject, and an electric field generated by the first sub-current within the subject intensify each other in the space between the first loop coil unit and the second loop coil unit. Simultaneously, the RF coil is also adjusted in a manner that a part of the second current passing through the second loop coil unit according to the signals detected by the second loop coil, flows into the first loop coil unit as the second sub-current, and an electric field generated by the second current within the subject, and an electric field generated by the second sub-current within the subject intensify each other in the space between the first loop coil unit and the second loop coil unit.

According to the present embodiment, noise correlation between the subcoils can be reduced. In addition, the first subcoil 410A and the second subcoil 410B can operate, being tuned to each other, whereby the sensitivity region is enlarged, allowing acquisition of high sensitivity. Consequently, the SNR of the composite image can be improved.

Second Embodiment

In the first embodiment and the example 1 thereof, there has been described that, upon receiving signals, the first sub-current being a part of the current of the signals detected by the first subcoil 410A as one of the two subcoils 410, passes through the second subcoil 410B, and the second sub-current being a part of the current of the signals detected by the second subcoil 410B passes through the first subcoil 410A.

In the present embodiment, adjustments are made in a manner that the current detected by the second subcoil 410B is prevented from flowing into the first subcoil 410A. In the present embodiment, the configuration of the array coil 400 is the same as that of the first embodiment, but an adjustment method is different in adjusting values of constituent circuit components (the adjustment inductor 441, the series capacitors 422, and the parallel capacitor 424).

Figure 14:
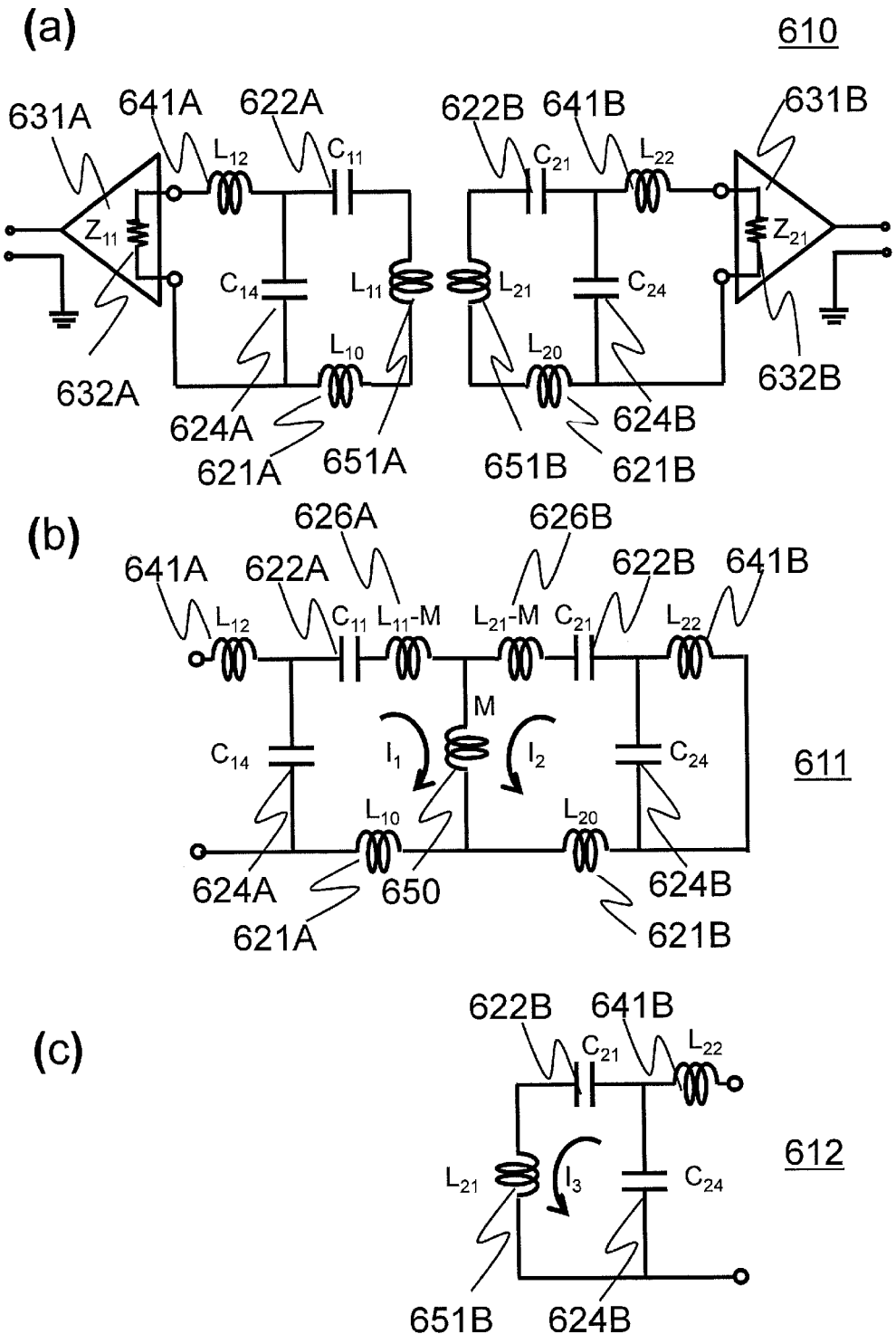
FIG. 14(a) illustrates an equivalent circuit of the array coil according to a second embodiment.
FIG. 14(b) illustrates the equivalent circuit looked at a low-impedance circuit side of the first subcoil side.
FIG. 14(c) illustrates the equivalent circuit looked at the low-impedance circuit side of the second subcoil side.

There will now be described the method for adjusting values of the circuit components according to the present embodiment, using the equivalent circuit 610 of the array coil 400 as shown in FIG. 14. In the following description, FIG. 6 and FIG. 9 are quoted as appropriate. In FIG. 14, the capacitors and values thereof, the inductors and values thereof, and the resonance frequency of each circuit are represented by the same reference numerals as those of the equivalent circuit 600 of the first embodiment as shown in FIG. 10.

In order to achieve both high sensitivity and multichannel, the circuit components constituting the array coil 400 are adjusted so that the following formulas 14 to 17 are satisfied.

$$f10 = f11 = f21 = f0 \tag{14}$$

$$f20 \neq f0 \tag{15}$$

$$\frac{1}{2\pi\sqrt{L_{12}C_{14}}} = f_0 \tag{16}$$

$$\frac{1}{2\pi\sqrt{L_{22}C_{24}}} \neq f_0 \tag{17}$$

It should be noted that each the frequencies is defined in the same manner as the first embodiment, and they are deigned as the following.
f0: frequency of the nuclear magnetic resonance
f10: resonance frequency of the L12C14 resonant circuit
f20: resonance frequency of the L22C24 resonant circuit
f11: resonance frequency of the first subcoil (the first resonator)
f21: resonance frequency of the second subcoil (the second resonator)

By adjusting the circuit components according to the formula 17, upon receiving signals, both ends of the capacitor 424B of the second subcoil 410B are prevented from being highly resistant, allowing the second subcoil 410B to be magnetically coupled with the first subcoil 410A.

FIG. 14(*b*) illustrates the equivalent circuit 611 of the first subcoil 410A, in the state that the first loop coil unit 420A and the second loop coil unit 420B are magnetically coupled according to the aforementioned adjustment. As illustrated in FIG. 14(*b*), upon receiving signals, the first loop coil unit 420A and the second loop coil unit 420B are magnetically coupled, and according to the signals detected by the first loop coil unit 420A, current I1 in a clockwise direction passes through the first loop coil unit 420A, and simultaneously, a part of the current I2 passes through the second loop coil unit 420B in a counterclockwise direction.

Furthermore, each of the circuit components is adjusted according to the formula 16, whereby both ends of the capacitor 424A of the first subcoil 410A become highly resistant, upon receiving signals, and thus the second subcoil 410B operates independently.

FIG. 14(c) illustrates the equivalent circuit 612 of the second resonator of the second subcoil 410B, when the second loop coil unit 420B operates independently according to the aforementioned adjustments. As illustrated in FIG. 14(c), upon receiving signals, the second resonator of the second subcoil 410B corresponds to the circuit 612 of the second loop coil unit 420B alone. Therefore, the current I3 that flows according to the second loop coil unit 420B never passes through the first loop coil unit 420A.

Then, each of the circuit components is adjusted according to the formula 14, whereby the resonance frequency f11 of the first resonator and the resonance frequency f22 of the second resonator, upon receiving signals, become equal to the nuclear magnetic resonance frequency f0. This allows the subcoil 410A and the subcoil 410B to detect the nuclear magnetic resonance signals.

Adjustment Example 2

There will be described an example where each of the circuit components is adjusted, setting the magnetic resonance frequency f0 to 64 MHz that corresponds to the nuclear magnetic resonance frequency of hydrogen in the static magnetic field strength of 1.5 T (tesla), in the array coil according to the second embodiment. It is to be noted that the shape and the size of the coil are the same as those of example 1 in the first embodiment.

Firstly, as in the case of the first embodiment (example 1), each of the circuit components is adjusted so that the equivalent circuits 611 and 612 as shown in FIGS. 14(b) and 14(c) respectively, resonate at 64 MHz, and the impedance at the both ends of the series circuit of the inductor 641A (L12) and the parallel capacitor 624A (C14) becomes 50Ω. Then, a value of the adjustment inductor 641 and a value of the parallel capacitor 624 are adjusted on the basis of the principle of the parallel resonant circuit characteristic, so that the aforementioned formulas 14 to 17 should be satisfied and the current upon coupling should flow in a desired manner.

Simultaneously, in order to achieve the current ratio of 10%, distance between the inductors 451B and 451A of the magnetic coupler 450 is made to vary, thereby adjusting the amount of electromagnetic coupling. It should be noted that the values of the inductors 451B and 451A are both 50 nH.

In the case of the present example 2, any of the first subcoil 410A and the second subcoil 410B may be adjusted first.

When the value of 52 MHz, smaller than f0, is used as f20, parameters after the adjustments are made as described above may be for example; C11=20.2 pF, C14=225 pF, C21=21 pF, C24=231 pF, L12=13.6 nH, L22=26 nH.

With the adjustments as described above, the array coil 400 of the present example may resonate at the nuclear magnetic resonance frequency, and the coil is allowed to receive nuclear magnetic resonance signals.

In the present example, the value of 52 MHz is used as the resonance frequency f20 of the L22C24 resonant circuit, when each of the circuit components is adjusted, but it is not limited to this example. Furthermore, a magnitude of difference between the resonant frequency f20 of the resonant circuit and f0 is not limited either, but it is desirable that the difference between the resonant frequency f20 of the L22C24 resonant circuit and f0 should be 10% or more. Furthermore, the current ratio of the sub-current is not limited to 10%, and as described in FIG. 13, the current ratio may be adjusted appropriately within the range from 5 to 30%, for instance, in accordance with the distance between the coils.

Further in the present example, there has been described that adjustments are made so that the current detected by the second coil is prevented from flowing into the first subcoil 410A, but it may be adjusted vice versa. In other words, the adjustments may also be made so that the current detected by the first subcoil 410A is prevented from flowing into the second subcoil 410B.

As described above, in the array coil of the present embodiment, the second subcoil 410B operates independently, whereas the first subcoil 410A is formed in a manner that a part of the current of signals detected by the first subcoil 410A is made to flow into the second subcoil 410B in the opposite direction. In other words, as shown in FIG. 6(c), the electric fields generated between the subcoils are adjusted so that they intensify each other. Noise correlation is obtained by the inner product of those electric fields. Therefore, when the inner product is obtained in each region, the region between the coils indicates a large negative value, relative to the other regions in the present embodiment as shown in the lower part of FIG. 6(c). In other words, the noise correlation is obtained by an integral of those values, and thus the noise correlation indicates a lower value with respect to the conventional method. Consequently, the noise correlation becomes smaller, and thereby improving the SNR of the composite image.

In addition, sensitivity distributions in the imaging areas in the subcoils are different from each other. Therefore, the array coil 400 of the present embodiment is allowed to operate as an array coil with a high sensitivity without reducing the number of channels. This configuration achieves an array coil with coils that provide a wide sensitivity region, even in a multichannel structure, and therefore, the array coil 400 of the present embodiment can implement all of the features, i.e., multichannel, wide sensitivity region, and low noise. In addition, since this configuration can be implemented by the arrangement of the subcoils 410 and adjustment of values of the circuit components, the structure thereof will never be complicated.

The first and second embodiments of the RF coil according to the present invention, and the examples thereof have been described so far. However, the RF coil of each embodiment is not limited to those in the figures and the aforementioned descriptions, and it may be modified variously. Representative modification examples will be described in the following.

<Modification Example of the Electromagnetic Coupler>

In the first embodiment, the electromagnetic coupler 450 comprises the inductor 451A and the inductor 451B, and the amount of coupling between the two subcoils is adjusted according to a positional relationship between those inductors. In the modification example, a magnetic coupling means may be employed as the electromagnetic coupler 450, instead of the pair of the inductors.

Figure 15:
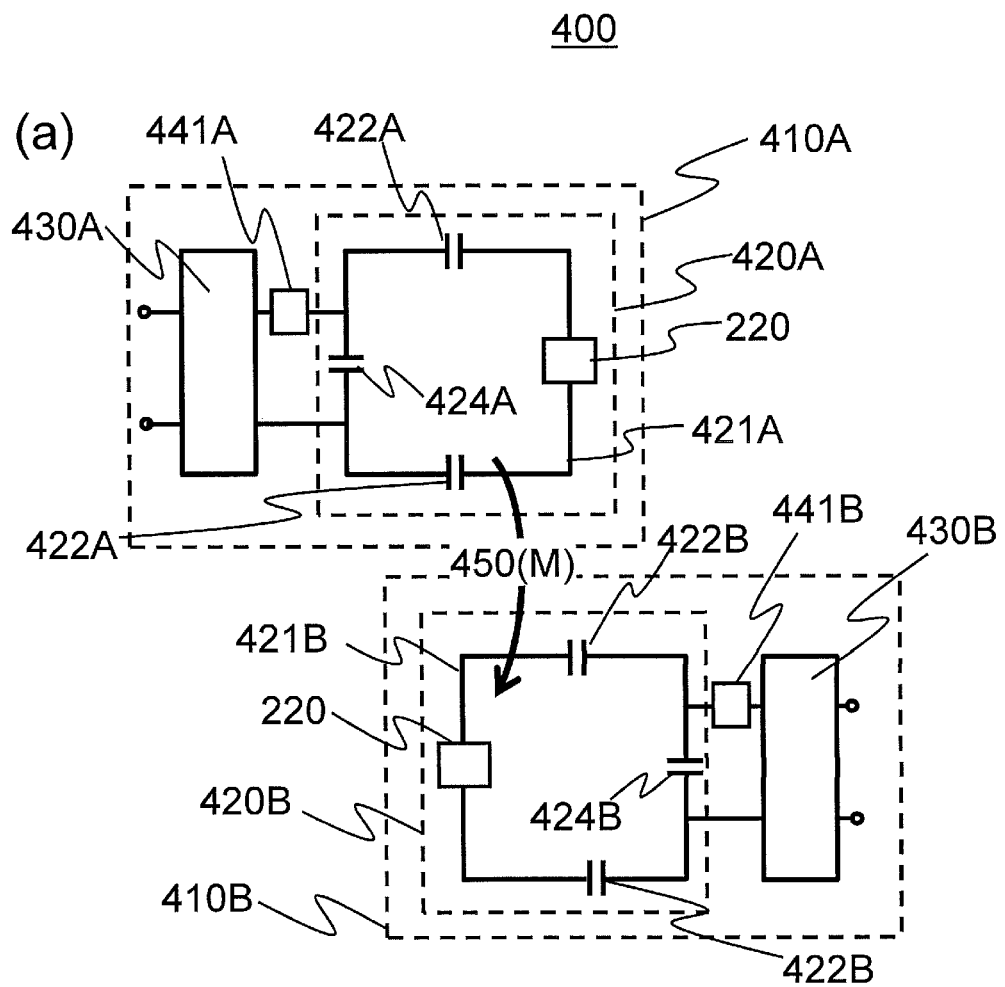
FIG. 15 illustrates a modification example of an electromagnetic coupler.

FIG. 15 shows a configuration of the array coil 400 according to the modification example. As illustrated, this array coil 400 is arranged in a manner that the first loop coil unit 420A is magnetically coupled with the second loop coil unit 420B, and the amount of coupling is adjusted. In order to adjust the amount of coupling according to the magnetic coupling means, a coupling inductor 451 (not illustrated in FIG. 15) may be arranged as a part of each of the loops 421, for example, and the magnetic coupling may be adjusted by using this coupling inductor. Alternatively, the inductor 451 may be installed on one subcoil only, out of the two subcoils.

Such coupling as described above may reduce the component count of the array coil, thereby holding down the cost in producing the array coil. In addition, since a loss generated in the inductors may also be reduced, the sensitivity is enhanced.

Figure 16:
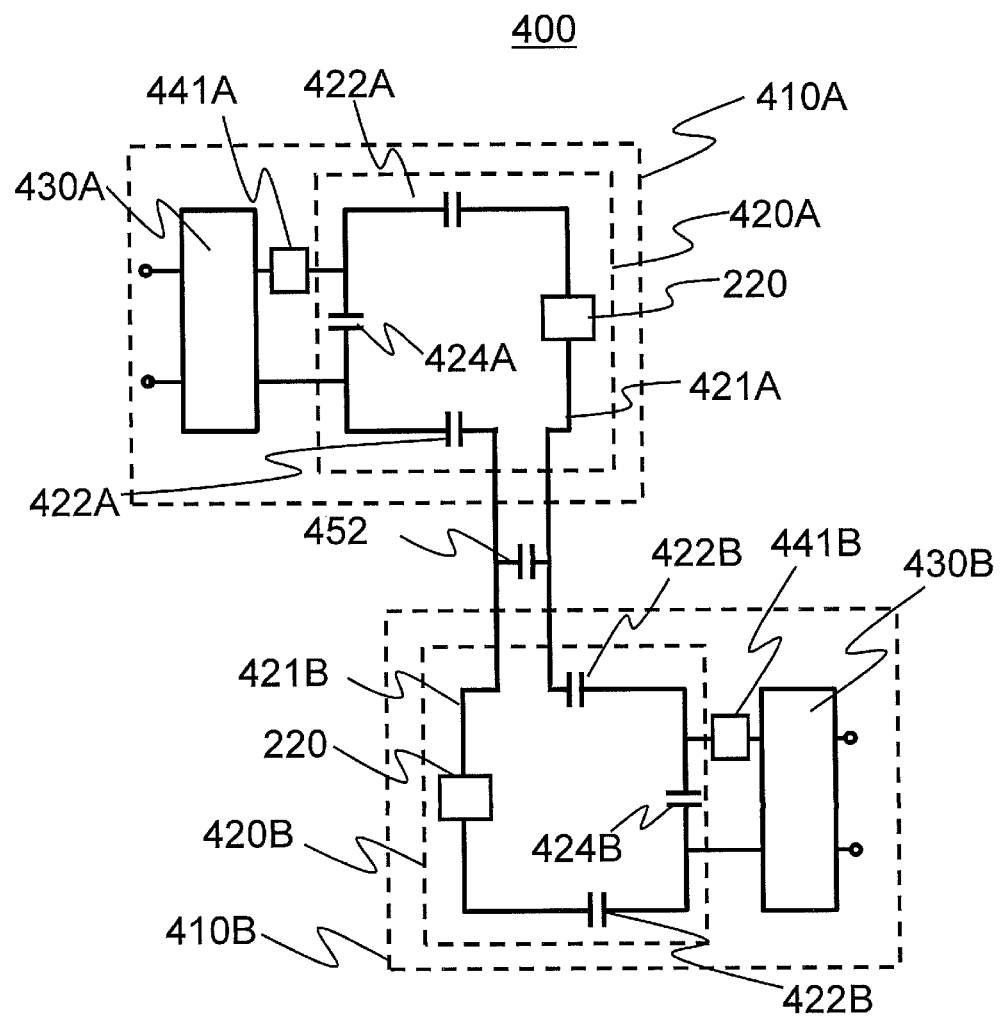
FIG. 16 is a schematic view showing another modification example of the electromagnetic coupler.

Furthermore, as shown in FIG. 16, for example, the two subcoils may be electrically coupled via a shared capacitor 452. The amount of coupling may be adjusted with the adjustment of the distance between coils and the value of the capacitor 452.

Such coupling as described above may reduce the component count of the array coil, thereby holding down the cost in producing the array coil. Furthermore, this configuration enables adjustments that are difficult with the use of the inductors.

Also in this modification example, as in the case of the first embodiment, the circuit components are adjusted so that each of the subcoils is allowed to receive nuclear magnetic resonance signals, and in addition, the circuit components are adjusted in a manner that a part of the current detected by one subcoil flows into the other subcoil in the form of sub-current, flowing in the opposite direction.

<Modification Example of Each Subcoil in Terms of its Shape and Others>

In the first and the second embodiments, there are described the cases where the first loop 421A and the second loop 421B of the same size and of the same shape are used. However, those loops may be different in shape and/or in size. Using the loops 421, different in shape and size may increase flexibility in arrangement patterns. Reduction of constraints in shape and/or in size of the loops 421 may facilitate adjustment of the magnitude of current that flows from one loop to the other loop, thereby reducing noise.

Subcoils in various shapes may be combined, thereby achieving an optimum coil that is suitable for the subject 103. There is a possibility that a current flow from one subcoil into the other subcoil increases mutual interference between the coils and accordingly, sensitivity may be lowered, but such desensitization can be controlled by using the subcoils in different sizes.

In the first and the second embodiments, there have been described examples where the shape of the loop 421 of each subcoil 410 is a rectangle on an approximate plane, or a single loop having a circular shape. However, the shape of the loop 421 is not limited to those examples as described above. Any shape is applicable as far as an equivalent circuit of the loop is comparable to the equivalent circuit 600.

Figure 17:
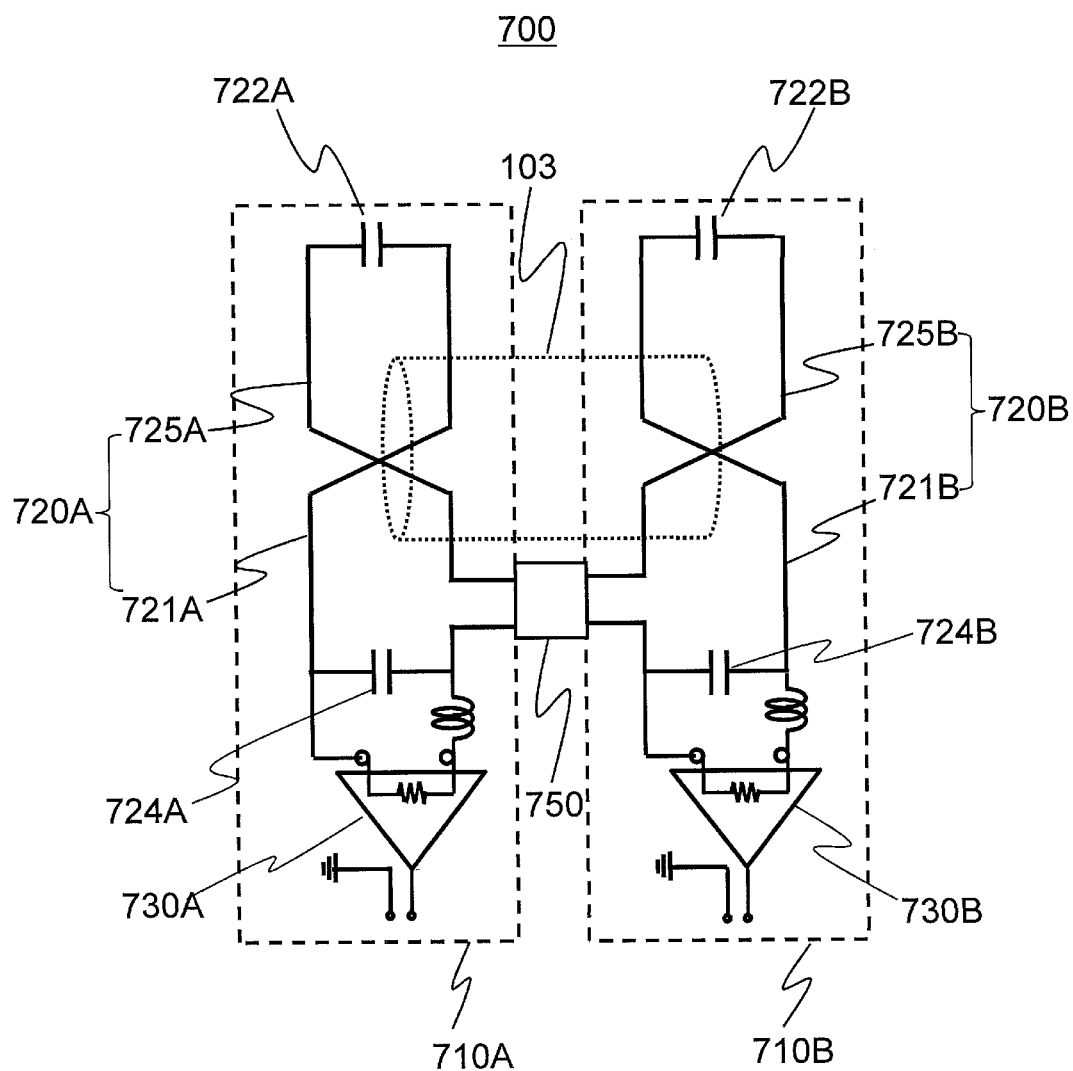
FIG. 17 is a schematic view showing a modification example of a loop coil unit.

By way of example, each of the first loop constituting the first subcoil and the second loop constituting the second subcoil may have a butterfly shape, placed on approximately the same plane. FIG. 17 illustrates an example of the array coil (butterfly array coil) 700 provided with the butterfly loops.

This array coil 700 is provided with the first subcoil 710A and the second subcoil 710B, each having the butterfly shape. The loop coil unit 720A constituting the first subcoil 710A has two loop sections 721A and 725A, and the loop coil unit 720B constituting the second subcoil 710B has two loop sections 721B and 725B. The parallel capacitors 724A and 724B are respectively inserted into one of the two loop sections, i.e., the loop sections 721A and 721B in the figure, and both ends of each of those loop sections are connected to the low-impedance signal processing circuit 730 in parallel. The series capacitors 722A and 722B, functioning as adjustment components, are inserted respectively into the loop sections 725A and 725B. Any number at least one may be applicable as the number of the capacitors, and it is not limited to the example as illustrated.

In addition, in the embodiment as illustrated, a coupler 750 for electromagnetically coupling the two subcoils 710A and 710B may be provided for coupling the loop section 721A with the loop section 721B. As in the case of either the first embodiment or the second embodiment, the electromagnetic coupler 750 may be the inductor 451 as shown in FIG. 9, or any other magnetic coupling means (as shown in FIG. 15 or FIG. 16, for example) may be applicable.

Also in this modification example, adjustments of the circuit components, distance of the electromagnetic coupler, and the like, may allow a part (e.g., 5% to 30%) of the current passing through the first subcoil 710A to flow into the second subcoil 710B, and the direction of the part of the current flowing into the second subcoil 710B should be opposite to the direction of the current passing through the first subcoil 710A.

The aforementioned adjustments may be made so that the formulas 4 to 8 or the formulas 14 to 17 are satisfied, as in the case of the first embodiment or the second embodiment. It should be noted that the loop shape and the mutual inductance of the array coil 700 are different from those of the array coil 400, and thus, values of the parallel capacitor, the series capacitor, and the adjustment inductor may be adjusted accordingly.

Similar to the array coil 400, the butterfly array coil 700 can be represented by the equivalent circuit 600 or 610 as shown in FIG. 10 or FIG. 14, and the operating principles are identical to those of the array coil 400. In other words, the loops 721A and 725A of the first subcoil 710A operate, being coupled with the loops 721B and 725B of the second subcoil 710B. When each of the circuit components are adjusted so that the formulas 4 to 8 are satisfied, a part of the current passing through the first subcoil 710A flows into the second subcoil 710B, and a part of the current passing through the second subcoil 810B flows into the first subcoil 710A. When each of the circuit components is adjusted so that the formulas 14 to 17 are satisfied, a part of the current passing through the first subcoil 710A flows into the second subcoil 710B, but the second subcoil 710B operates independently. Alternatively, a part of the current passing through the second subcoil 710B flows into the first subcoil 710A, but the first subcoil 710A operates independently.

Also in the butterfly array coil 700 of the modification example, according to the adjustments as described above, each subcoil 710 is provided with sensitivity against nuclear magnetic resonance signals from the detection target. The loop 721A of the first subcoil 710A allows the sub-current to pass through the loop 721B of the second subcoil 710B via the electromagnetic coupler 750, and thus the electric fields generated between the coils intensify each other, whereby noise correlation is reduced and the SNR is enhanced.

In addition, since the butterfly array coil 700 has the loops 721, 725 in the butterfly shape, it is possible to detect magnetic resonance signals not only from the surface of the subject 103, but also from a region in the depth direction with high sensitivity.

In the array coil 700 as shown in FIG. 17, loops having the same shape and size are used respectively for the first loop coil unit 720A and the second loop coil unit 720B. However, those loops may be different in shape and/or in size. Using the loops different in shape and size respectively for the first subcoil 710A and the second subcoil 710B may increase flexibility in arrangement patterns. In addition, this may facilitate adjustment of the magnitude of magnetic coupling.

In addition, also in the modification example, any of the applicable modification examples of the first embodiment and the second embodiment may be appropriately combined and employed.

Third Embodiment

In the first and the second embodiments, there have been described the cases where two subcoils are combined to constitute the array coil. In the present embodiment, three or more subcoils are combined to constitute the array coil. With this configuration, both multiple channels and low noise can be implemented. In addition, this configuration achieves more enhanced or enlarged sensitivity.

The MRI apparatus of the present embodiment has basically the same configuration as the MRI apparatus 100 of the first embodiment. There will now be described the present embodiment, focusing on the points that are different from the first embodiment.

Figure 18:
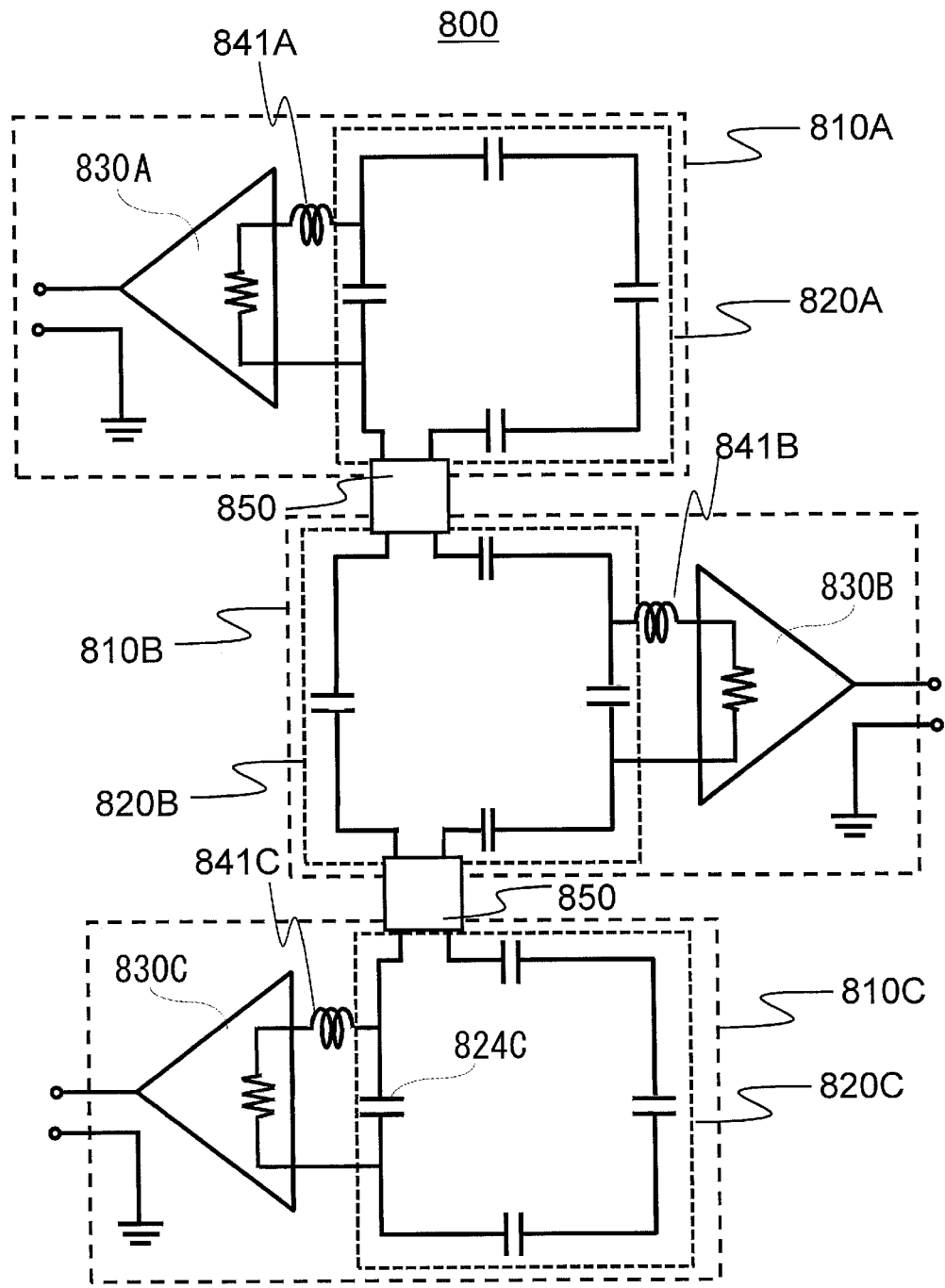
FIG. 18 schematically illustrates the array coil according to a third embodiment.

FIG. 18 illustrates the array coil 800 according to the present embodiment. As illustrated, the array coil 800 of the present embodiment comprises a first subcoil 810A, a second subcoil 810B, and a third subcoil 810C. Those subcoils 810A, 810B, and 810C are arranged in this order, and adjacent subcoils 810 are placed, being connected via electromagnetic couplers 850. Each of the first, the second, and the third subcoils 810 is connected to the receiver 162 via the low-impedance signal processing circuit 830, and those subcoils constitute one receive channel.

The configurations of each of the first subcoil 810A and the third subcoil 810C are the same as the first subcoil 410A of the first embodiment (FIG. 9). The second subcoil 810B is the same as the second subcoil 410B of the first embodiment. Capacitors and inductors of each subcoil are adjusted so that the following formulas 18 to 21 are satisfied, as in the case of the first embodiment.

$$f11 = f21 = f31 = f0 \quad (18)$$

$$f10 \neq f0, \frac{1}{2\pi\sqrt{L_{12}C_{14}}} \neq f_0 \quad (19)$$

$$f20 \neq f0, \frac{1}{2\pi\sqrt{L_{22}C_{24}}} \neq f_0 \quad (20)$$

$$f30 \neq f0, \frac{1}{2\pi\sqrt{L_{32}C_{34}}} \neq f_0 \quad (21)$$

Definitions of respective frequencies are the same as those of the first embodiment as the following:
f0: nuclear magnetic resonance frequency
f10: resonance frequency of the L12C14 resonant circuit in the first subcoil;
f20: resonance frequency of the L22C24 resonant circuit in the second subcoil;
f30: resonance frequency of the L32C34 resonant circuit in the third subcoil;
f11: resonance frequency of the first subcoil (the first resonator)
f21: resonance frequency of the second subcoil (the second resonator)
f31: resonance frequency of the third subcoil (the third resonator)

The resonance frequency of the third subcoil indicates the resonance frequency of the third subcoil 810C (the third resonator) excluding the low-impedance signal processing circuit 830, looked at the low-impedance signal processing circuit 830 of the third subcoil 810C. The L32C34 resonant circuit is a parallel resonant circuit of the parallel capacitor 824C inserted into the loop coil unit 820C of the third subcoil 810, and the magnetic coupling adjuster 841C (inductor 841C), and the value of the parallel capacitor 824C is represented by C34, and the value of the inductor 841C is represented by L32.

With those adjustments as described above, the array coil 800 of the present embodiment is adjusted so that a part of the current of the signals detected by the first subcoil 810A and a part of the current of the signals detected by the second subcoil 810B respectively are allowed to flow into each other, and a part of the current of the signals detected by the third subcoil 810C and a part of the current of the signals detected by the second subcoil 810B are allowed to flow into each other. In addition, each of the subcoils is also adjusted to resonate at the nuclear magnetic resonance frequency f0.

For example, the magnetic resonance frequency f0 is set to be the nuclear magnetic resonance frequency of 64 MHz of hydrogen in the static magnetic field strength 1.5 T (tesla). Then, the circuit components of the first subcoil 810A, the circuit components of the second subcoil 810B, and the circuit components of the third subcoil 810C are adjusted so that the L12C14 resonant circuit, the L22C24 resonant circuit, and the L32C34 resonant circuit should not resonate at the nuclear magnetic resonance frequency. In other words, the adjustments are made so that those resonant circuits may not become highly resistant, upon receiving signals at this nuclear magnetic frequency.

The loop coil unit 820A of the first subcoil 810A allows a part of the signals detected by the subcoil 810A to flow into the loop coil unit 820B of the second subcoil 810B, according to the loop coil unit 820B of the second subcoil 810B and the electromagnetic coupler 850, upon receiving signals. This is because each of the circuit components of the second subcoil 810B is adjusted according to the aforementioned formula 20, thereby preventing high resistance upon receiving signals.

On the other hand, the first loop coil unit 820A is hardly magnetically coupled with the loop coil unit 820C of the third subcoil 810C, nor vice versa. This is because both are separated in some distance away, and coupling is dominant between the adjacent coils.

Similarly, the loop coil unit 820C of the third subcoil 810C allows a part of the signals detected by the subcoil 810C to flow into the loop coil unit 820B of the second subcoil 810B, according to the loop coil unit 820B of the second subcoil 810B and the electromagnetic coupler 850, upon receiving signals. This is because each of the circuit components of the second subcoil 810B is adjusted according to the aforementioned formula 20, preventing high resistance upon receiving signals.

In addition, as for the second subcoil 810B, a part of the signal detected by the subcoil 810B upon receiving signals is allowed to flow into the loop coil unit 820C of the third subcoil 810C and into the loop coil unit 820A of the first subcoil 810A, respectively according to the two electromagnetic couplers 850 provided in the loop coil unit 820B. This is because the circuit components in the first subcoil 810A and the third subcoil 810C are adjusted respectively according to the formulas 19 and 21, thereby preventing high resistance upon receiving signals.

With the configuration above, the array coil 800 of the present embodiment forms a current path having the figure-of-eight shape in the first loop coil unit 820A and in the second loop coil unit 820B, upon receiving signals by the first subcoil 810A. In addition, upon receiving signals by the third subcoil 810C, a current path having the figure-of-eight shape is formed in the third loop coil unit 820C and in the second loop coil unit 820B. As thus described, the subcoils 810 send and receive the current mutually between the adjacent subcoils, so as to form the current paths each having the figure-of-eight shape, and intensify each other the electric fields generated between the coils. Therefore, noise correlation is reduced and the SNR is enhanced. In addition, each of the subcoils 810 resonates at the nuclear magnetic resonance frequency of a detection target. Therefore, each of the subcoils 810 is allowed to acquire nuclear magnetic resonance signals of the detection target.

As described so far, according to the receiver RF coil of the present embodiment, a wide sensitivity region and low noise can be achieved, as in the case of the other embodiments. In particular, increasing the number of subcoils may ensure much larger sensitivity region.

<Modification Example of the Third Embodiment>

The array coil of the present embodiment is not limited to the example as shown in FIG. 18, and it may be modified variously.

[Modification Example of the Magnetic Coupling]

In the present embodiment, each of the circuit components is adjusted in a manner that, upon receiving signals, the first subcoil 810A and the second subcoil 810B mutually send and receive current, and the third subcoil 810C and the second subcoil 810B mutually send and receive current.

However, the pattern of the magnetic coupling is not limited to this configuration. For example, the circuit components may be adjusted so that each of the first subcoil 810A and the third subcoil 810C is magnetically coupled with the second subcoil 810B, and the second subcoil 810B is made independent, without any coupling.

[Modification Example of the Number and Arrangement of the Subcoils]

In the present embodiment, there has been described the example where the three subcoils 810A, 810B, and 810C are combined. However, the number of the subcoils 810 is not limited to this number. It is further possible to use four or more subcoils 810 (e.g., FIG. 8(c)). Increasing the number of subcoils 810 may provide sensitivity in a much wider area.

Figure 19:
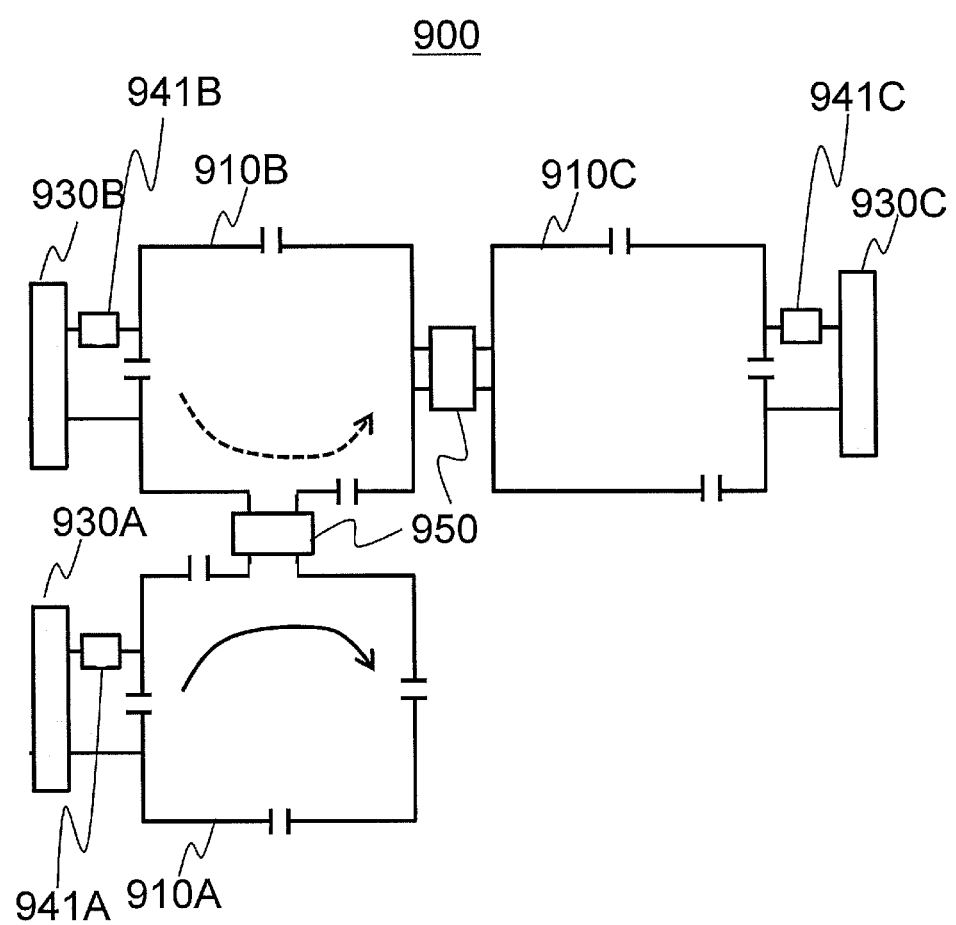
FIG. 19 illustrates a modification example of the array coil according to the third embodiment.

When the number of the subcoils (the number of channels) is increased, the array coil of the example as shown in FIG. 18 may be extended in the longitudinal direction. Alternatively, like the multichannel coil 900 as shown in FIG. 19, for example, the layout direction of the subcoils 910 may be varied. In this case, the subcoil 910A and the subcoil 910C positioned on the ends may be or may not be coupled via the electromagnetic coupler 950. In addition, as a pattern of the magnetic coupling, it may be arranged one-directionally or bi-directionally in the array.

Furthermore, in the present embodiment, the coils coupled via the electromagnetic coupler 950 are adjacent to each other, but the configuration is not limited to this example. Another subcoil may be inserted between some of the subcoils, or between all of the subcoils. With this configuration, density of the coil arrangement becomes higher, thereby raising the sensitivity. In addition, flexibility in designing the sensitivity region can be enhanced.

Figure 20:
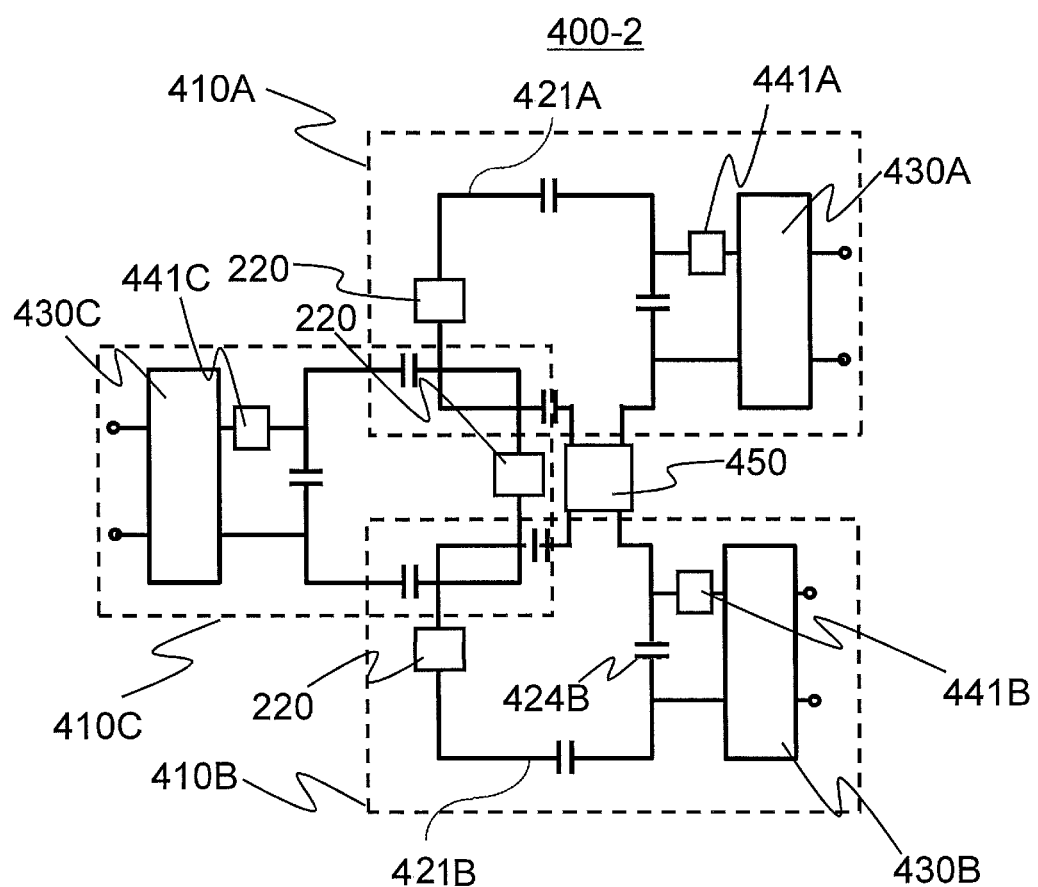
FIG. 20 illustrates another modification example of the array coil according to the third embodiment.

FIG. 20 illustrates an example of the multichannel coil where a third subcoil is placed between two subcoils being electromagnetically coupled, and the third subcoil is not electromagnetically coupled therewith.

In the multichannel coil 400-2 as illustrated, two subcoils 410A and 410B are coupled via the electromagnetic coupler 450, constituting the array coil, and each of the circuit components is adjusted similar to the array coil 400 of the first embodiment or the second embodiment.

The third subcoil 410C is placed between the loop 421A of the first subcoil 410A and the loop 421B of the second subcoil 410B, and the third subcoil is not magnetically coupled with those two subcoils. Upon receiving signals by the first subcoil 410A or upon receiving signals by the second subcoil 410B in the multichannel coil 400-2, that is, upon receiving signals by at least either one of the subcoils, there occurs a flow of current in the shape of figure-of-eight, and this is similar to the array coil 400 of the first embodiment or the second embodiment.

As described so far, the two loops 421A and 421B being electromagnetically coupled are not necessarily adjacent to each other, and arranging the third sub coil therebetween may enhance a density of the RF coil arrangement. This allows improvement of the sensitivity.

In addition, the modification examples as described in the first and the second embodiments may be applicable to the present embodiment. By way of example, the shape of the loop coil unit in each subcoil may be a shape other than the rectangle, and the size and shape may be different as to each subcoil. The electromagnetic coupler 450, the magnetic coupling adjuster 441 and others, may also be configured variously.

DESCRIPTION OF SYMBOLS

090: coordinate system, 100: MRI apparatus, 101: MRI apparatus, 102: table, 103: subject, 110: magnet, 111: magnet, 121: shim coil, 122: shim power source, 131: gradient magnetic field coil, 132: gradient magnetic field power source, 140: sequencer, 151: transmit RF coil, 152: RF magnetic field generator, 161: receiver RF coil, 162: receiver, 170: computer, 171: monitor, 180: magnetic coupling prevention circuit driver, 210: transmit-receive magnetic coupling prevention circuit, 211: PIN diode, 212: control signal line, 220: transmit-receive magnetic coupling prevention circuit, 220m: transmit-receive magnetic coupling prevention circuit, 221: PIN diode, 221m: cross diode, 222: inductor, 223: control signal line, 300: birdcage RF coil, 301: linear conductor, 302: end conductor, 303: capacitor, 311: input port, 312: input port, 400: array coil, 400-1: array coil, 410: subcoil, 420: loop coil unit, 421: loop, 422: series capacitor, 423: capacitor, 424: parallel capacitor, 430: low-impedance signal processing circuit, 431: low-input impedance signal amplifier, 441: magnetic coupling adjuster, 450: electromagnetic coupler, 451: coupling inductor, 462: coil part, 463: coil part, 500: parallel resonant circuit, 501: capacitor, 502: inductor, 600: equivalent circuit, 601: equivalent circuit, 602: equivalent circuit, 610: equivalent circuit, 611: equivalent circuit, 612: equivalent circuit, 621: inductor, 622: series capacitor, 624: parallel capacitor, 626: inductor, 627: inductor, 632: impedance, 641: adjustment inductor, 700: butterfly array coil, 710: subcoil, 720: loop coil unit, 721: loop, 725: loop, 730: low-impedance signal processing circuit, 750: electromagnetic coupler, 800: array coil, 810: subcoil, 820: loop coil unit, 830: low-impedance signal processing circuit, 841: adjustment inductor, 850: electromagnetic coupler, 900: array coil, 910: subcoil, 920: loop coil unit, 921: loop, 930: low-impedance signal processing circuit, 941: magnetic coupling adjuster, 950: electromagnetic coupler

What is claimed is:

1. An RF coil comprising,
a first subcoil having a first loop coil unit made of a conductor, being capable of receiving nuclear magnetic resonance signals from a subject,
a second subcoil having a second loop coil unit made of the conductor, being capable of receiving the nuclear magnetic resonance signals from the subject, and
an electromagnetic coupler placed between the first subcoil and the second subcoil, and configured to couple the first subcoil and the second subcoil electromagnetically, wherein,
adjustments are made in a manner that a part of a first current passing through the first loop coil unit, according to signals detected by the first loop coil unit, is made to flow into the second loop coil unit in the form of a first sub-current, and an electric field generated in the subject by the first current and an electric field generated in the subject by the first sub-current intensify each other in a space between the first loop coil unit and the second loop coil unit.

2. The RF coil according to claim 1, wherein,
adjustments are made in a manner that a part of a second current passing through the second loop coil unit, according to signals detected by the second loop coil unit, is made to flow into the first loop coil unit in the form of a second sub-current, and an electric field generated in the subject by the second current and an electric field generated in the subject by the second sub-current intensify each other in the space between the first loop coil unit and the second loop coil unit.

3. The RF coil according to claim 1, wherein,
adjustments are made in a manner that the second current passing through the second loop coil unit according to the signals detected by the second loop coil unit is prevented from flowing into the first loop coil unit.

4. The RF coil according to claim 1, wherein,
the electromagnetic coupler is a magnetic coupler comprising an inductor.

5. The RF coil according to claim 1, wherein,
the electromagnetic coupler is an electric coupler via a conductor.

6. The RF coil according to claim 1, wherein,
the electromagnetic coupler performs electromagnetic coupling according to a positional relationship between the first loop coil unit and the second loop coil unit.

7. The RF coil according to claim 1, wherein,
at least one of the first and second subcoils further comprises a magnetic coupling adjuster configured to connect a loop coil unit of the at least one subcoil with a low impedance signal processing circuit that is connected to the at least one subcoil, wherein,
the magnetic coupling adjuster comprises at least one of a capacitor and an inductor as an adjusting circuit component, and
the loop coil unit comprises:
a series capacitor inserted in series with an inductor component of the loop coil unit, and
a parallel capacitor inserted in series with the inductor component, rendering the loop coil unit to serve as a parallel resonant circuit, and
wherein the at least one subcoil is adjusted by adjusting values of the adjusting circuit component, the series capacitor, and the parallel capacitor.

8. The RF coil according to claim 7, wherein,
a phase difference between the first current and the first sub-current is larger than 90 degrees and smaller than 270 degrees.

9. The RF coil according to claim 7, wherein,
strength of the first sub-current is between 5% and 30% of the strength of the first current.

10. The RF coil according to claim 1, wherein,
at least one of the first loop coil unit and the second loop coil unit is a loop having a butterfly shape.

11. The RF coil according to claim 1, further comprising,
a third subcoil electromagnetically coupled with at least one of the first subcoil and the second subcoil.

12. The RF coil according to claim 1, further comprising,
a third subcoil between the first subcoil and the second subcoil, without any magnetically coupling therewith.

13. A magnetic resonance imaging apparatus, comprising,
a static magnetic field former configured to form a static magnetic field,
a gradient magnetic field former configured to form a gradient magnetic field,
a transmit RF coil configured to apply an RF magnetic field to a subject placed in the static magnetic field,
a receiver RF coil configured to detect nuclear magnetic resonance signals from the subject, and
a signal processor configured to process the nuclear magnetic resonance signals detected by the receiver RF coil, wherein,
the receiver RF coil is the RF coil according to claim 1.

14. The magnetic resonance imaging apparatus according to claim 13, wherein,
the RF coil is arranged in a manner that the first loop coil unit and the second loop coil unit are placed along a plane that is orthogonal to the static magnetic field.

15. The magnetic resonance imaging apparatus according to claim 13, wherein,
the RF coil is arranged in a manner that the first loop coil unit and the second loop coil unit are placed along a plane that is parallel to the static magnetic field.

* * * * *